(12) United States Patent
Mototsu et al.

(10) Patent No.: US 8,007,722 B2
(45) Date of Patent: Aug. 30, 2011

(54) ANALYZER

(75) Inventors: Kazunori Mototsu, Kobe (JP);
Tomoyuki Nishida, Ashiya (JP);
Toshihiro Ootani, Kobe (JP); Kazuya Fukuda, Kobe (JP); Motoki Koyama, Kobe (JP)

(73) Assignee: Sysmex Corporation, Kobe (JP)

( * ) Notice: Subject to any disclaimer, the term of this patent is extended or adjusted under 35 U.S.C. 154(b) by 461 days.

(21) Appl. No.: 11/973,717

(22) Filed: Oct. 9, 2007

(65) Prior Publication Data

US 2008/0085215 A1    Apr. 10, 2008

(30) Foreign Application Priority Data

Oct. 10, 2006   (JP) .................................. 2006-276537

(51) Int. Cl.
*G01N 31/00* (2006.01)
*G01N 21/00* (2006.01)
*G01N 15/06* (2006.01)

(52) U.S. Cl. ................. 422/64; 422/63; 422/65; 422/67; 422/68.1

(58) Field of Classification Search ...................... 422/64
See application file for complete search history.

(56) References Cited

U.S. PATENT DOCUMENTS

| 5,827,479 | A | * | 10/1998 | Yamazaki et al. | 422/67 |
| 2004/0057872 | A1 | * | 3/2004 | Shibuya et al. | 422/64 |
| 2005/0095724 | A1 | * | 5/2005 | Shibutani et al. | 436/180 |
| 2007/0172390 | A1 | * | 7/2007 | Ootani et al. | 422/64 |
| 2008/0063570 | A1 | * | 3/2008 | Fujino et al. | 422/99 |

FOREIGN PATENT DOCUMENTS

| JP | H04-36658 | 2/1992 |
| JP | 2005-37171 | 2/2005 |

* cited by examiner

*Primary Examiner* — Brian J Sines
*Assistant Examiner* — Jennifer Wecker
(74) *Attorney, Agent, or Firm* — Brinks Hofer Gilson & Lione

(57) ABSTRACT

An analyzer comprising: a reagent suction unit for suctioning reagent from a reagent container; an analyzing unit for analyzing an analyzing specimen comprising a sample and the reagent; a container raising and lowering unit comprising a mounting platform, wherein the container raising and lowering unit is configured to raise and lower the mounting platform; and a container holder configured to hold a plurality of reagent containers, wherein the container holder comprises a reagent container holding portion; wherein the mounting platform is configured to move a reagent container mounted thereon from a first position to a plurality of second positions, wherein the plurality of second positions comprises a position at which the reagent container is in contact with the reagent container holding portion is disclosed.

19 Claims, 24 Drawing Sheets

ANALYZER

RELATED APPLICATIONS

This application claims priority under 35 U.S.C. §119 to Japanese Patent Application No. 2006-276537 filed Oct. 10, 2006, the entire content of which is hereby incorporated by reference.

FIELD OF THE INVENTION

The present invention relates to analyzers, in particular, to an analyzer equipped with a container holder for holding reagent containers.

BACKGROUND

Conventionally, an analyzer for suctioning a reagent from a plurality of reagent containers mounted on a reagent table and analyzing a sample is known. The user needed to remove the reagent container to be replaced from the reagent table and mount a new reagent container to a predetermined position of the reagent table in such analyzer when reagent replacement was necessary. However, the user had to put his/her hand inside the accommodating unit of the reagent container in such analyzer, and thus the replacement task of the reagent was troublesome.

An analyzer that facilitates reagent replacement by the user is thus known (see e.g., Japanese Laid-Open Patent Publication No. 4-36658 and Japanese Laid-Open Patent Publication No. 2005-37171).

An analyzer including a rotatable reagent storage in which reagent bottles are arranged, a reagent bottle supply mechanism for supplying the reagent bottle to the reagent storage, and a reagent bottle discharge mechanism for discharging the reagent bottle from the reagent storage is disclosed in Japanese Laid-Open Patent Publication No. 4-36658. Such analyzer enables automatic replacement of the reagent bottle during analysis.

An analyzer including a reagent disc for installing a reagent, a replenishing reagent cabinet arranged at a position different from the reagent disc, and a reagent holding means for conveying the reagent from the replenishing reagent cabinet to the reagent disc is disclosed in Japanese Laid-Open Patent Publication No. 2005-37171. Such analyzer facilitates reagent replacement.

However, the analyzer disclosed in Japanese Laid-Open Patent Publication No. 4-36658 has a complicating configuration since a belt line mechanism for conveying the reagent from a reagent bottle set yard to the reagent storage, and a belt line mechanism for conveying the reagent from the reagent storage to a reagent bottle discharge yard are necessary. Furthermore, in the analyzer disclosed in Japanese Laid-Open Patent Publication No. 4-36658, a space for arranging the reagent bottle set yard, the belt line mechanisms, and the reagent bottle discharge yard is necessary, which enlarges the device.

The analyzer disclosed in Japanese Laid-Open Patent Publication No. 2005-37171 has a complicating configuration since a mechanism (reagent holding means) for conveying the reagent in three-dimensional directions (XYZ directions) is necessary to convey the reagent from the replenishing reagent cabinet to the reagent disc. Furthermore, in the analyzer disclosed in Japanese Laid-Open Patent Publication No. 2005-37171, a space for arranging the reagent holding means and the replenishment reagent cabinet is necessary, which enlarges the device.

SUMMARY OF THE INVENTION

The scope of the present invention is defined solely by the appended claims, and is not affected to any degree by the statements within this summary.

A first aspect of the present invention is an analyzer comprising: a reagent suction unit for suctioning reagent from a reagent container; an analyzing unit for analyzing an analyzing specimen comprising a sample and the reagent; a container raising and lowering unit comprising a mounting platform, wherein the container raising and lowering unit is configured to raise and lower the mounting platform; and a container holder configured to hold a plurality of reagent containers, wherein the container holder comprises a reagent container holding portion; wherein the mounting platform is configured to move a reagent container mounted thereon from a first position to a plurality of second positions, wherein the plurality of second positions comprises a position at which the reagent container is in contact with the reagent container holding portion A second aspect of the present invention is an analyzer comprising: a reagent suction unit for suctioning reagent from a reagent container; an analyzing unit for analyzing an analyzing specimen comprising a sample and the reagent; a container holder configured to hold a plurality of reagent containers in a circular ring form; a container raising and lowering unit configured for executing a mounting operation of mounting the reagent container on the container holder by lowering the reagent container, and a raising operation of raising the reagent container to a retrieving position above the container holder; and a rotation unit configured for moving at least one of the plurality of reagent containers to a raise waiting position, at which the reagent container starts rising, by rotating the plurality of reagent containers held by the container holder.

A third aspect of the present invention is an analyzer comprising: a reagent suction unit for suctioning reagent from a reagent container; an analyzing unit for analyzing an analyzing specimen comprising a sample and the reagent; a container holder configured to hold a plurality of reagent containers; a mounting platform on which at least one of the plurality of reagent containers is mounted; and a driving source for moving the mounting platform to a first position, above the container holder, at which a reagent container is mounted and retrieved, and a second position, below the first position, at which a reagent container is held by the container holder.

DETAILED DESCRIPTION OF THE PREFERRED EMBODIMENTS

The preferred embodiments of the present invention will be described hereinafter with reference to the drawings.

An overall configuration of an immune analyzer 1 according to one embodiment of the present invention will now be described with reference to FIGS. 1 to 6.

The immune analyzer 1 according to one embodiment of the present invention is an apparatus for carrying out examinations on various items such as hepatitis B, hepatitis C, tumor marker, and thyroid hormone using samples such as blood. In the immune analyzer 1, magnetic particles (R2 reagent) are bonded to a trapped antibody (R1 reagent) bonded to an antigen contained in a sample such as blood, which is the measuring object, and thereafter, the bound antigen, trapped antibody, and magnetic particles are attracted to a magnet (not shown) of a BF (Bound Free) separator 14 (see FIGS. 1 and 2) to remove the R1 reagent containing non-reactive (free) trapped body. A labeled antibody (R3 reagent) is bonded to the antigen bound with magnetic particles, and thereafter, the bound magnetic particles, antigen, and labeled antibody are attracted to a magnet of a BF separator 14 to remove a R3 reagent containing non-reactive (free) labeled antibody. Furthermore, a light emitting substrate (R5 reagent) that emits light in the reaction process with the labeled antibody is added, and a light emitting amount generated through the reaction of the labeled antibody and the light emitting substrate is measured. After such processes, the antigen or the antibody contained in the sample that bonds with the labeled antibody is quantitatively measured.

Figure 1:
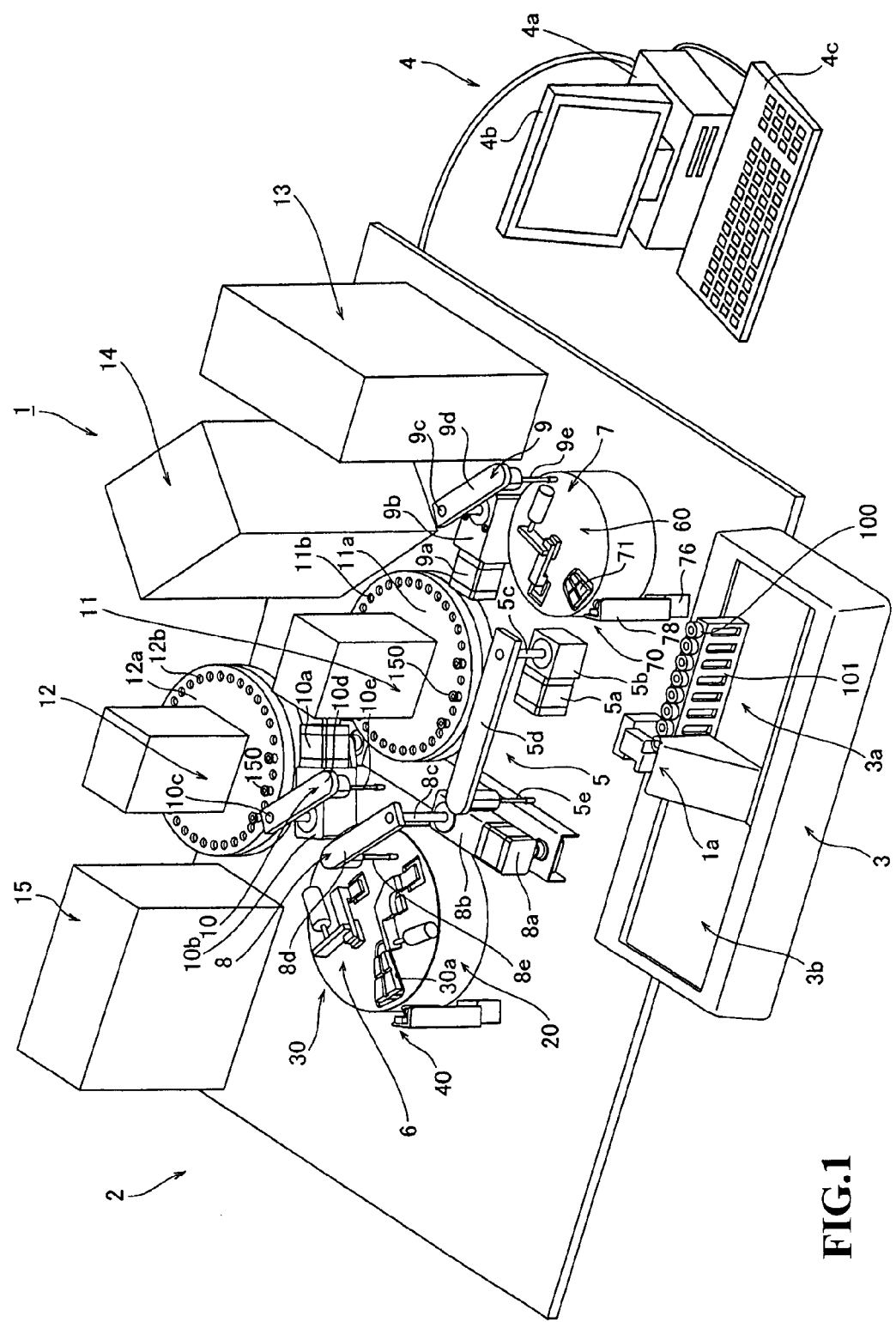
FIG. 1 is a perspective view showing an overall configuration of an immune analyzer according to one embodiment of the present invention.
Figure 2:
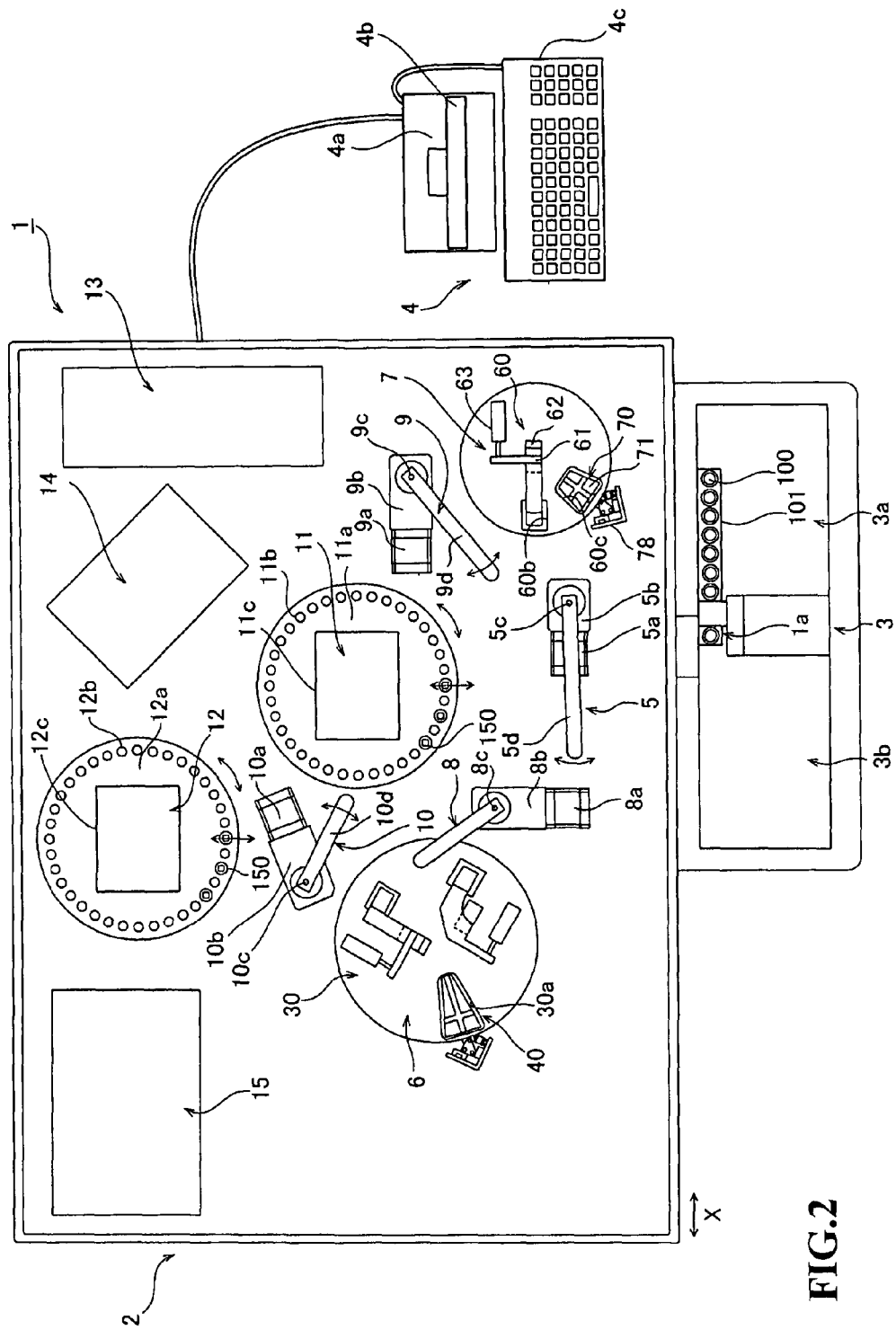
FIG. 2 is a plan view of the immune analyzer shown in FIG. 1.
Figure 3:
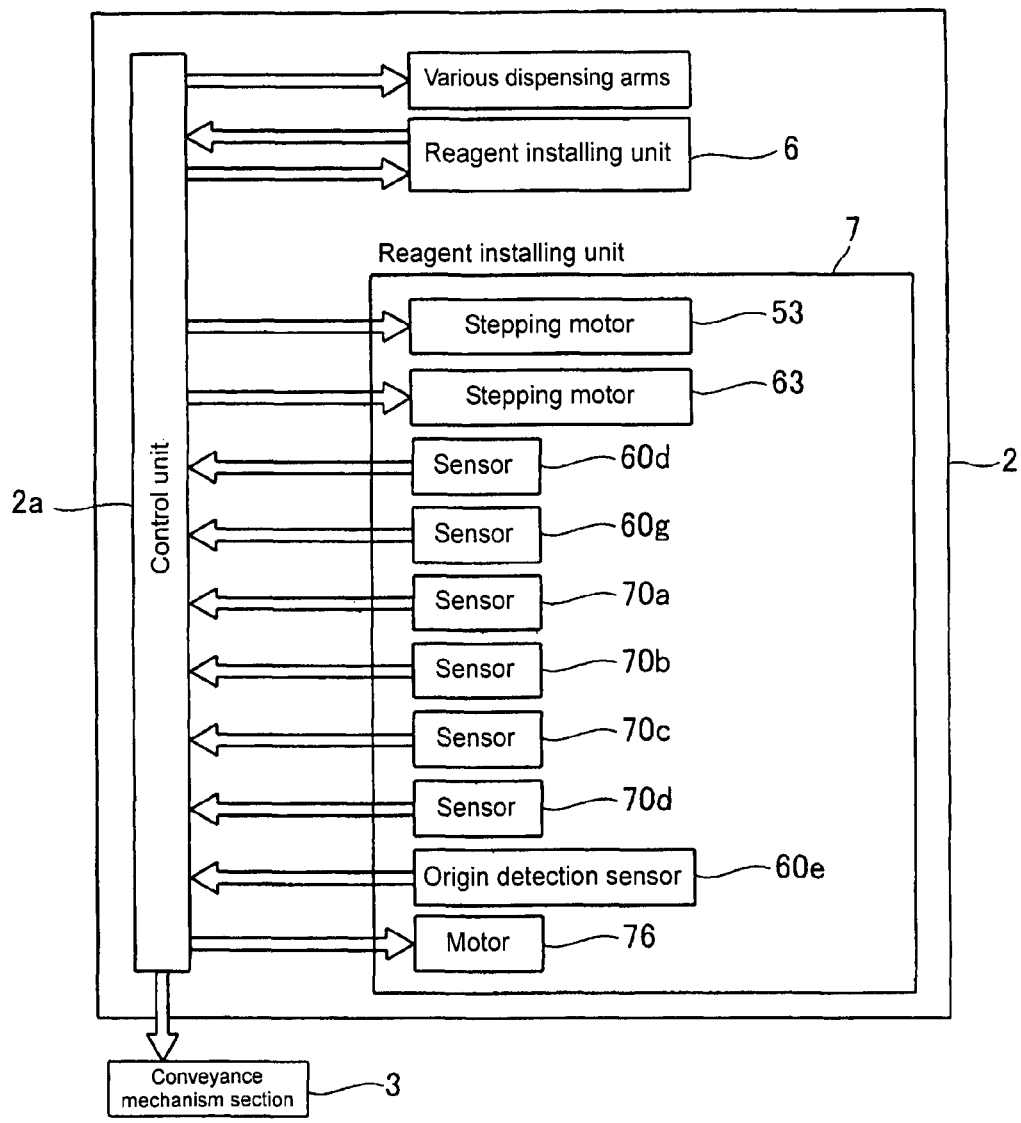
FIG. 3 is a block diagram including a control unit of a measurement mechanism section of the immune analyzer according to one embodiment of the present invention.
Figure 4:
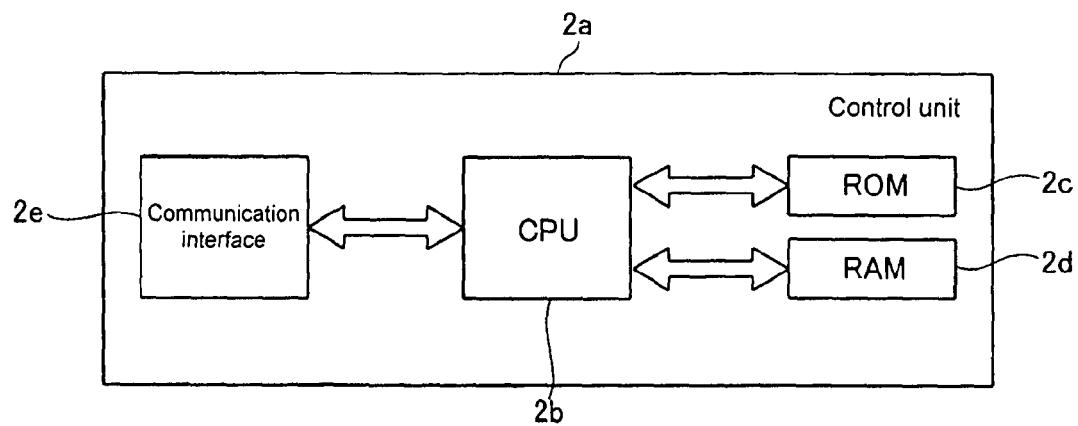
FIG. 4 is a block diagram showing a configuration of the control unit of the measurement mechanism section shown in FIG. 3.

As shown in FIGS. 1 and 2, the immune analyzer 1 includes a measurement mechanism section 2, a sample conveyance section (sampler) 3 arranged on the front surface side of the measurement mechanism section 2, and a control device 4 including PC (personal computer) electrically connected to the measurement mechanism section 2. The measurement mechanism section 2 is configured by a sample dispensing arm 5, reagent installing units 6 and 7, reagent dispensing arms 8, 9, and 10, a primary reaction unit 11 and a secondary reaction unit 12, a cuvette supplying unit 13, a BF separator 14, and a detector 15. As shown in FIG. 3, each mechanism (various dispensing arms, reagent installing unit 6, and reagent installing unit 7, and the like) in the measurement mechanism section 2 are controlled by a control unit 2a arranged in the measurement mechanism section 2. Specifically, the control unit 2a receives signals of various sensors (sensors 60d, 60g, 70a, 70b, 70c, 70d, and origin detection sensor 60e, and the like) arranged in the reagent installing unit 7, and controls the drive of various driving sources (stepping motors 53, 63, and motor 76, and the like) arranged in the reagent installing unit 7. The conveyance mechanism section 3 is also controlled by the control unit 2a. The various dispensing arms, various sensors, and various driving sources will be described in detail below.

The control unit 2a is mainly configured by a CPU 2b, a ROM 2c, a RAM 2d, and a communication interface 2e.

The CPU 2b executes computer programs stored in the ROM 2c and the computer programs read by the RAM 2d. The ROM 2c stores computer programs executed by the CPU 2b, data used in executing the computer program, and the like. The RAM 2d is used to read out the computer program stored in the ROM 2c. In executing the computer program, the ROM 2c is used as a work region of the CPU 2b.

The communication interface 2e is connected to the control device 4, and transmits optical information (data of received light amount generated by reaction of the labeled antibody and light emitting substrate) of the sample to the control device 4, and receives signals from the control unit 4a of the control device 4. The communication interface 2e has a function of transmitting a command from the CPU 2b for driving each unit of the conveyance mechanism section 3 and the measurement mechanism section 2.

As shown in FIGS. 1 and 2, the sample conveyance section 3 is configured to convey a rack 101 mounted with a plurality of test tubes 100 accommodating the sample to a position corresponding to a suction position 1a at where the sample dispensing arm 5 suctions the sample. The sample conveyance section 3 includes a rack set part 3a for setting the rack 101 in which the test tubes 100 accommodating non-processed sample are mounted, and a rack storing part 3b for storing the rack 101 in which the test tubes 100 accommodating the dispensing processed sample are mounted. The test tube 100 accommodating the non-processed sample is conveyed to a position corresponding to the suction position 1a of the sample dispensing arm 5, so that the sample dispensing arm 5 suctions the sample such as blood in the test tube 100, and thereafter, the rack 101 mounted with the test tube 100 is stored in the rack storing part 3b.

The control device 4 (FIG. 1) consists of a personal computer (PC), and includes a control unit 4a including CPU, ROM, RAM, a display unit 4b and a keyboard 4c. The display unit 4b is arranged to display result of analysis obtained by analyzing data of digital signals transmitted from a detector 15. In the present embodiment, instruction for replacement, addition, and retrieval of a reagent-containing assembly 300, to be hereinafter described, can be carried out in the control device 4.

Figure 5:
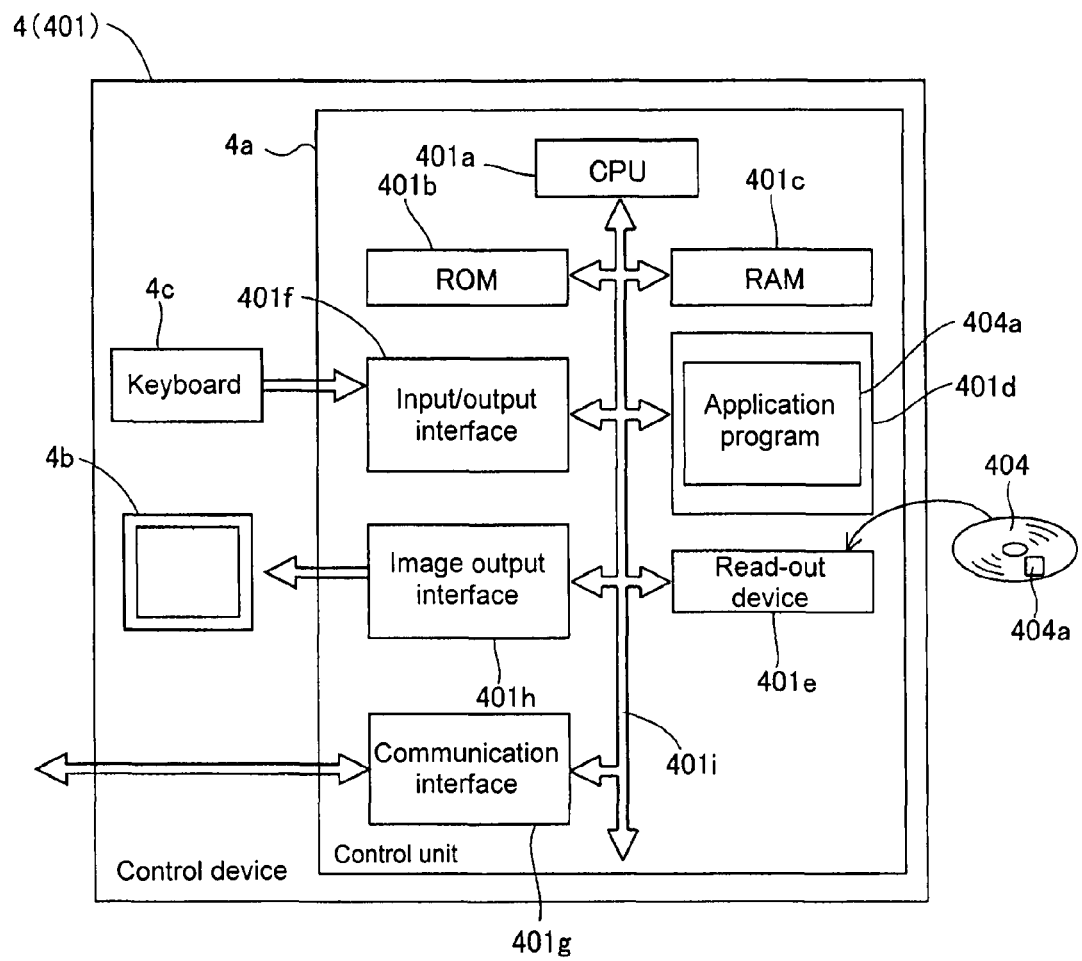
FIG. 5 is a block diagram showing a control device of the immune analyzer according to one embodiment of the present invention.

The configuration of the control device 4 will now be described. As shown in FIG. 5, the control device 4 is configured by a computer 401 mainly consisting of the control unit 4a, the display unit 4b, and the keyboard 4c. The control unit 4a is mainly configured by a CPU 401a, a ROM 401b, a RAM 401c, a hard disc 401d, a read-out device 401e, an input/output interface 401f, a communication interface 401g, and an image output interface 401h. The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 4 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs to be executed by the CPU 401a such as operating system and application program, as well as data used in executing the computer program. The immune analysis application program 404a according to the present embodiment is also installed in the hard disc 401d.

The read-out device 401e is configured by flexible disc drive, CD-ROM drive, DVD-ROM drive, and the like, and is able to read out computer programs and data recorded on a portable recording medium 404. The immune analysis application program 404a is stored in the portable recording medium 404, where the computer 401 reads out the application program 404a from the portable recording medium 404, and installs the application program 404a to the hard disc 401d.

The application program 404a is not only provided by the portable recording medium 404, but also provided through communication line (wired or wireless) from external devices communicatably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows (registered trademark) manufactured and sold by US Microsoft Co. is installed in the hard disc 401d. In the following description, the application program 404a according to the first embodiment is assumed to operate on the operating system.

The output interface 401f is configured by serial interface such as USB, IEEE1394, RS-232C; parallel interface such as SCSI, IDE, IEEE1284; analog interface such as D/A converter, A/D converter, and the like. The keyboard 4c is connected to the input/output interface 401f, so that the user can input data to the computer 401 using the keyboard 4c.

The communication interface 401g is, for example, Ethernet (registered trademark) interface. The computer 401 transmits and receives data with the measurement mechanism section 2 using a predetermined communication protocol by means of the communication interface 401g.

The image output interface 401h is connected to the display unit 4b configured by LCD, CRT, or the like, and is configured to output an image signal corresponding to the image data provided from the CPU 401a to the display unit 4b. The display unit 4b displays the image (screen) according to the input image signal.

The immune analysis application program 404a installed in the hard disc 401d of the control unit 4a measures the amount of antigen or antibody in the measurement specimen using the received light amount (data of digital signal) of the measurement specimen transmitted from the detector 15 of the measurement mechanism section 2.

The sample dispensing arm 5 (see FIGS. 1 and 2) has a function of dispensing the sample in the test tube 100 conveyed to the suction position 1a by the sample conveyance section 3 into a cuvette 150 held by a holder 11b of a rotatable table 11a of the primary reaction unit 11 to be hereinafter described. As shown in FIGS. 1 and 2, the sample dispensing arm 5 includes a motor 5a, a drive transmitting part 5b connected to the motor 5a, and an arm 5d attached to the drive transmitting part 5b by way of a shaft 5c. The drive transmitting part 5b is configured to turn the arm 5d with the shaft 5c as the center by the driving force from the motor 5a, and move the arm in the up and down direction (Z direction). A pipette 5e for suctioning and discharging the sample is arranged at the distal end of the arm 5d.

The reagent installing unit 6 (see FIGS. 1 and 2) is arranged to install the reagent-containing assembly for holding a reagent container in which an R1 reagent containing trapped antibody is accommodated and a reagent container in which a R3 reagent containing labeled antibody is accommodated. As shown in FIG. 1, the reagent installing unit 6 includes a reagent holder 20 for holding the reagent-containing assembly, a lid 30 attached to the reagent holder 20, and a raising and lowering unit 40 for replacing the reagent-containing assembly in the reagent holder 20 through a hole 30a formed in the lid 30.

The reagent installing unit 7 (see FIGS. 1 and 2) is arranged to install a reagent-containing assembly 300 (see FIG. 6) for holding a test container in which a R2 reagent containing magnetic particles is accommodated. The configuration of the reagent installing unit 7 will be hereinafter described in detail.

The reagent dispensing arm 8 (see FIGS. 1 and 2) has a function of suctioning the R1 reagent in the reagent-containing assembly installed in the reagent installing unit 6 and dispensing the suctioned R1 reagent into the cuvette 150 dispensed with the sample of the primary reaction unit 11. The reagent dispensing arm 8 includes a motor 8a, a drive transmitting part 8b connected to the motor 8a, and an arm 8d attached to the drive transmitting part 8b by way of a shaft 8c. The drive transmitting part 8b is configured to turn the arm 8d with the shaft 8c as the center by the driving force from the motor 8a, and move the arm in the up and down direction. A pipette 8e (see FIG. 1) for suctioning and discharging the R1 reagent in the reagent-containing assembly is arranged at the distal end of the arm 8d. That is, the pipette 8e is configured to suction the R1 reagent in the reagent-containing assembly installed in the reagent installing unit 6, and thereafter, dispense the suctioned R1 reagent into the cuvette 150 dispensed with the sample of the primary reaction unit 11.

The reagent dispensing arm 9 (see FIGS. 1 and 2) has a function of dispensing the R2 reagent in the reagent-containing assembly 300 installed in the reagent installing unit 7 into the cuvette 150 dispensed with the sample and the R1 reagent of the primary reaction unit 11. The reagent dispensing arm 9 includes a motor 9a, a drive transmitting part 9b connected to the motor 9a, and an arm 9d attached to the drive transmitting part 9b by way of a shaft 9c. The drive transmitting part 9b is configured to turn the arm 9d with the shaft 9c as the center by the driving force from the motor 9a, and move the arm in the up and down direction. A pipette 9e (see FIG. 1) for suctioning and discharging the R2 reagent in the reagent-containing assembly 300 is arranged at the distal end of the arm 9d. Thus, the pipette 9e is configured to suction the R2 reagent in the reagent-containing assembly 300 installed in the reagent installing unit 7, and thereafter, dispense the suctioned R2 reagent into the cuvette 150 dispensed with the sample and the R1 reagent of the primary reaction unit 11.

The reagent dispensing arm 10 (see FIGS. 1 and 2) has a function of suctioning the R3 reagent in the reagent-containing assembly installed in the reagent installing unit 6, and dispensing the suctioned R3 reagent into the cuvette 150 dispensed with the sample, the R1 reagent, and the R2 reagent of the secondary reaction unit 12. The reagent dispensing arm 10 includes a motor 10a, a drive transmitting part 10b connected to the motor 10a, and an arm 10d attached to the drive transmitting part 10b by way of a shaft 10c. The drive transmitting part 10b is configured to turn the arm 10d with the shaft 10c as the center by the driving force from the motor 10a, and move the arm in the up and down direction. A pipette 10e (see FIG. 1) for suctioning and discharging the R3 reagent in the reagent-containing assembly is arranged at the distal end of the arm 10d. That is, the pipette 10e is configured to suction the R3 reagent in the reagent-containing assembly installed in the reagent installing unit 6, and thereafter, dispense the suctioned R3 reagent into the cuvette 150 dispensed with the sample, the R1 reagent, and the R2 reagent of the secondary reaction unit 12.

As shown in FIGS. 1 and 2, the primary reaction unit 11 is arranged to rotatably transfer the cuvette 150 held by the holder 11b of the rotatable table 11a by a predetermined angle for every predetermined period (18 seconds in the present embodiment), and to stir the sample, the R1 reagent, and the R2 reagent in the cuvette 150. That is, the primary reaction unit 11 is arranged to react the R2 reagent containing magnetic particles and the antigen in the sample in the cuvette 150. The primary reaction unit 11 is configured by a rotatable table 11a for conveying the cuvette 150 accommodating the sample, the R1 reagent, and the R2 reagent in the rotating direction, and a container conveying part 11c for stirring the sample, R1 reagent, and R2 reagent in the cuvette 150 and conveying the cuvette 150 accommodating the stirred sample, R1 reagent and R2 reagent to the BF separator 14 (see FIGS. 1 and 2) to be hereinafter described.

The rotatable table 11a is configured so as to rotatably transfer the cuvette 150 held in the holder 11b by a predetermined angle every 18 seconds. Thus, various devices (sample dispensing arm 5, reagent dispensing arms 8 and 9 etc.) of the immune analyzer 1 are controlled so as to operate on the cuvette 150 at the predetermined transferred position at a timing the cuvette is transferred to the predetermined position by the rotatable table 11a.

The container conveying part 11c is rotatably arranged at the central portion of the rotatable table 11a. The container conveying part 11c has a function of gripping the cuvette 150 held in the holder 11b of the rotatable table 11a and stirring the sample in the cuvette 150. Furthermore, the container conveying part 11c has a function of transferring the cuvette 150 accommodating the specimen obtained by stirring and incubating the sample, the R1 reagent and the R2 reagent to the BF separator 14 (see FIGS. 1 and 2).

The secondary reaction unit 12 (see FIGS. 1 and 2) has a configuration similar to the primary reaction unit 11, and is arranged to rotatably transfer the cuvette 150 held by the holder 12b of the rotatable table 12a by a predetermined angle for every predetermined period (18 seconds in the present embodiment), and to stir the sample, the R1 reagent, the R2 reagent, the R3 reagent, and the R5 reagent in the cuvette 150. That is, the secondary reaction unit 12 is arranged to react the R3 reagent containing labeled antibody and the antigen in the sample in the cuvette 150, and to react the R5 reagent containing light emitting substrates and the labeled antibody of the R3 reagent. The R5 reagent is dispensed into the cuvette 150 accommodating the sample, the R1 reagent, the R2 reagent, and the R3 reagent of the secondary reaction unit 12 by a R5 reagent dispensing arm (not shown) arranged near the secondary reaction unit 12. The secondary reaction unit 12 is configured by a rotatable table 12a for conveying the cuvette 150 accommodating the sample, the R1 reagent, the R2 reagent, the R3 reagent, and the R5 reagent in the rotating direction, and a container conveying part 12c for stirring the sample, the R1 reagent, the R2 reagent, R3 reagent, and the R5 reagent in the cuvette 150 and conveying the cuvette 150 accommodating the stirred sample etc. to the BF separator 14. The container conveying part 12c has a function of again conveying the cuvette 150 processed by the BF separator 14 to the holder 12b of the rotatable table 12. The detailed structure of the secondary reaction unit 12 is similar to the primary reaction unit 11, and thus the description thereof will be omitted.

The cuvette supplying unit 13 (see FIGS. 1 and 2) is configured to sequentially supply a plurality of cuvettes 150 to the holder 11b of the rotatable table 11a of the primary reaction unit 11.

The BF separator 14 has a function of separating the non-reacting R1 reagent (unnecessary component) and the magnetic particles from the specimen in the cuvette 150 conveyed by the container conveying part 11c of the primary reaction unit 11, and a function of separating the non-reacting R3 reagent (unnecessary component) and the magnetic particles from the specimen in the cuvette 150 (see FIG. 1) conveyed by the container conveying part 12c of the secondary reaction unit 12.

The detector 15 (see FIGS. 1 and 2) is arranged to measure the amount of antigen contained in a sample by acquiring the light generated in the reaction process of the labeled antibody bound to the antigen of the sample performed with a predetermined process and the light emitting substrate with a photo multiplier tube.

The structure of the reagent installing unit 7 of the immune analyzer 1 and the reagent-containing assembly 300 installed in the reagent installing unit 7 according to one embodiment of the present invention will now be described with reference to FIGS. 6 to 18.

Figure 6:
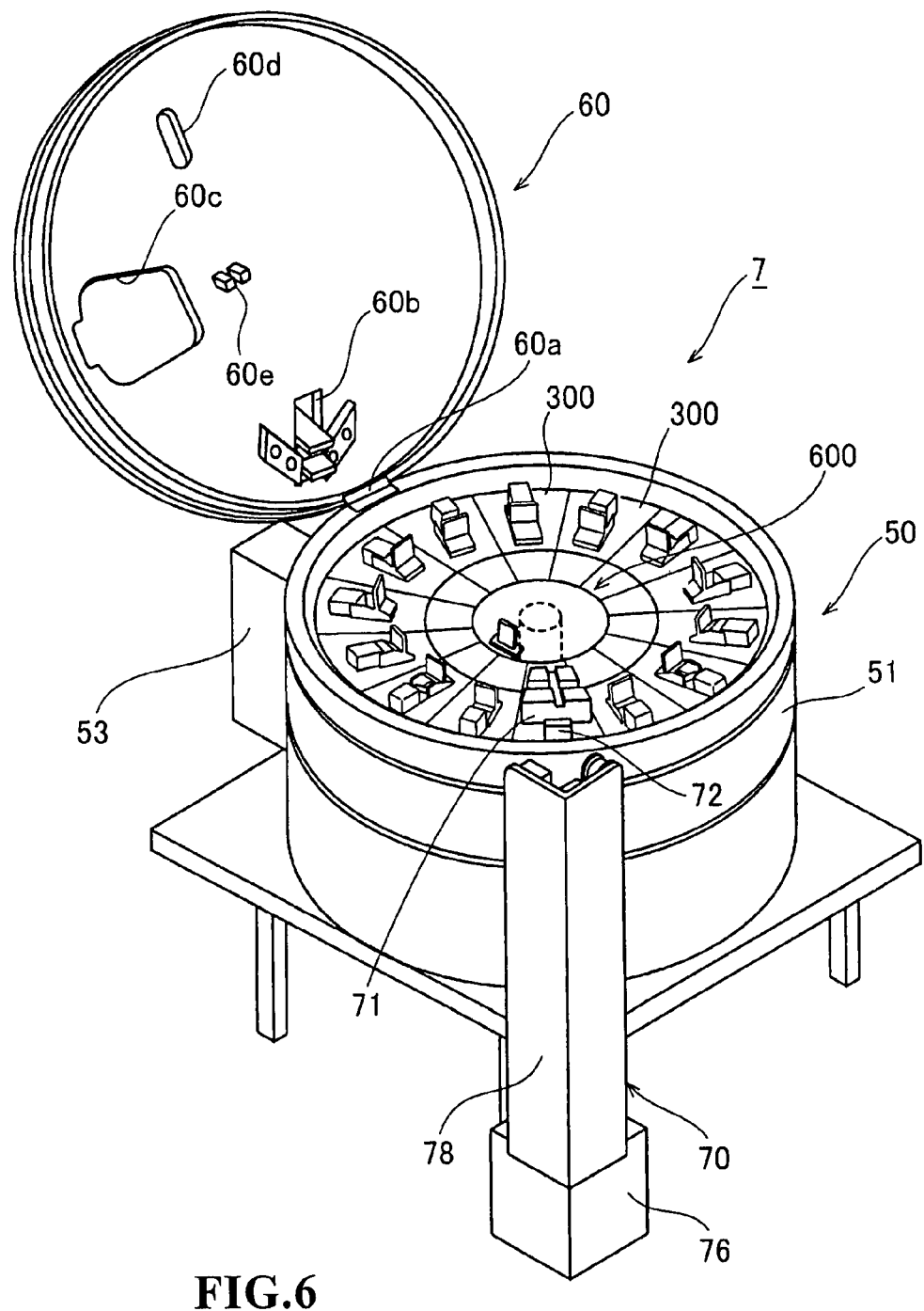
FIG. 6 is a perspective view showing an overall configuration of a reagent installing unit shown in FIG. 1.

As shown in FIG. 6, the reagent installing unit 7 includes a reagent holder 50 of cylindrical shape for holding the reagent-containing assembly 300 in a circular ring form, a lid 60 attached to the reagent holder 50 in an openable and closable manner, and a raising and lowering unit 70 attached to the side surface (outer wall part 51) of the cylindrical reagent holder 50. A Peltier element (not shown) is also attached at the bottom of the reagent installing unit 7, and the inside of the reagent installing unit 7 is maintained at about 15° C.

Figure 7:
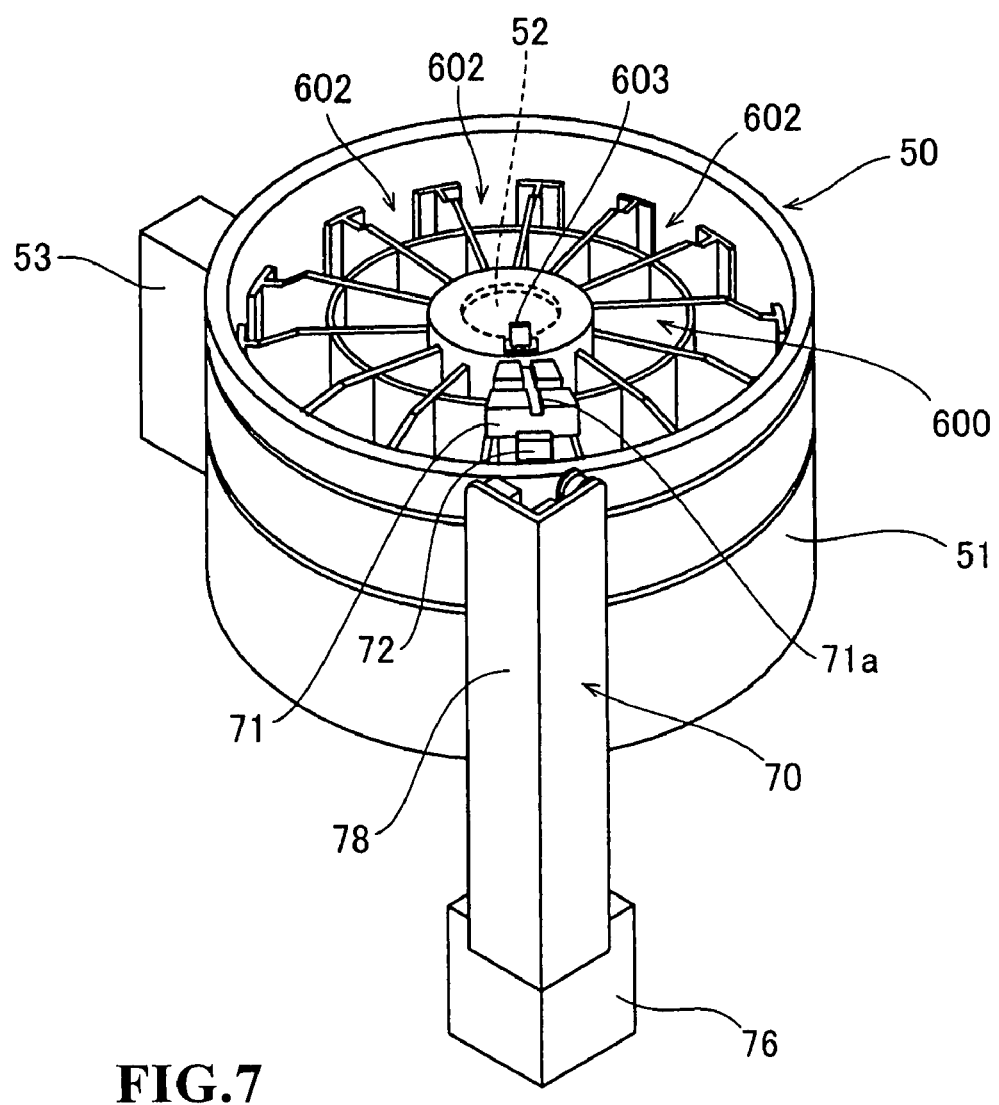
FIG. 7 is a perspective view showing a reagent holder of the reagent installing unit shown in FIG. 6.
Figure 8:
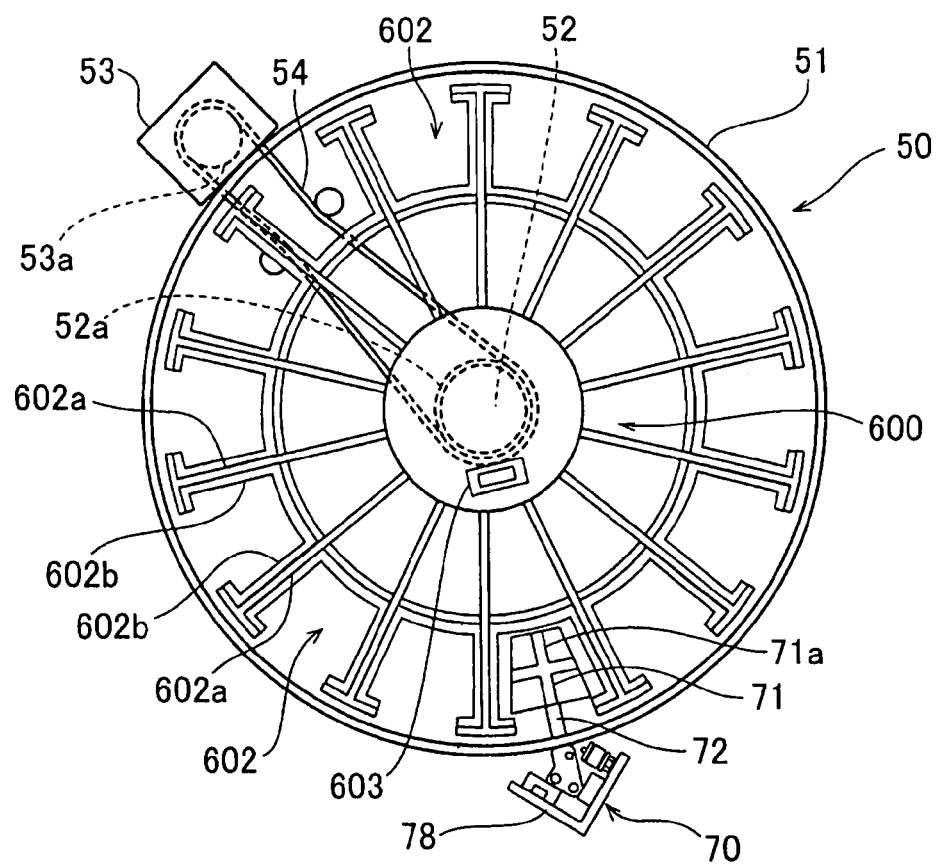
FIG. 8 is a plan view of the reagent holder of the reagent installing unit shown in FIG. 7.

As shown in FIGS. 7 and 8, the reagent holder 50 includes a cylindrical outer wall part 51, a rotatable rotation shaft 52 arranged at the center, a stepping motor 53 for rotating the rotation shaft 52, and a belt 54 for transmitting the driving force of the stepping motor 53 to the rotation shaft 52 (see FIG. 8). A heat insulating material (not shown) is attached over the entire surface on the inner surface of the outer wall part 51, so that the temperature inside the reagent holder 50 is maintained at low temperature (about 15° C.). As shown in FIG. 8, the driving force of the stepping motor 53 is transmitted to the rotation shaft 52 via the belt 54 by a pulley 53a that rotates by the stepping motor 53 and a pulley 52a coaxially fixed to the rotation shaft 52.

Figure 9:
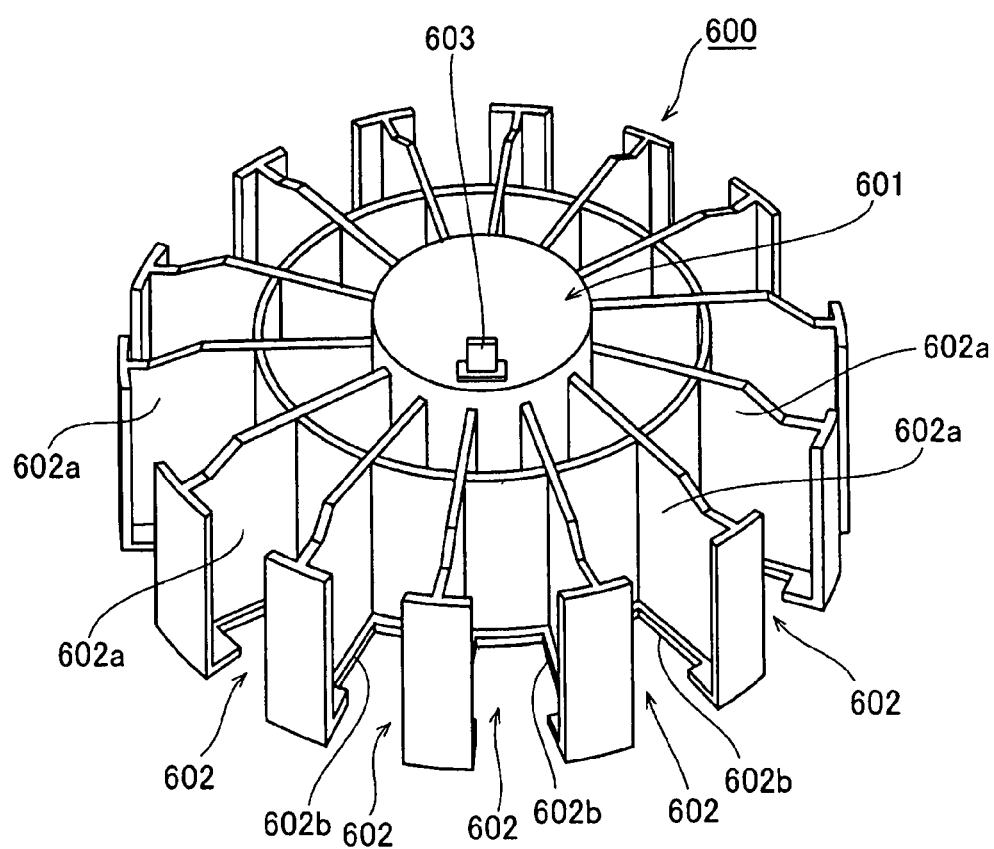
FIG. 9 is a perspective view showing a rack for holding the reagent-containing assembly used in the immune analyzer according to one embodiment of the present invention.

A rack 600 for holding a plurality of reagent-containing assemblies 300 in a circular ring form is fixedly attached to the rotation shaft 52. The rack 600 holding the reagent-containing assemblies 300 rotates when the rotation shaft 52 is rotated with the reagent-containing assemblies 300 held in the rack 600, and thus the reagent-containing assembly 300 holding the reagent to be suctioned can be moved to below a hole 60b and an input/output hole 60c of the lid 60 to be hereinafter described. As shown in FIG. 9, the rack 600 includes an inserting part 601, formed at the center of the rack 600, to which the rotation shaft 52 is inserted; a plurality of holders 602, formed in a circular ring form with the inserting part 601 as the center, for holding the reagent-containing assembly 300, and an origin detection strip 603 arranged so as to project above the inserting part 601. The holder 602 is configured by a partition plate 602a and a supporting part 602b. The partition plate 602a is arranged in plurals at a predetermined angular interval so as to radially extend from the inserting part 601. The supporting part 602b is arranged at the lower part of the portions facing each other of the partition plates 602a and at the lower part of the inserting part 601 so as to project to the inner side. Each reagent-containing assembly 300 is arranged such that the peripheral edge of the bottom 323 (see FIG. 18) is supported by the supporting part 602b in a space defined by a pair of partition plates 602a. Furthermore, as shown in FIG. 8, the upper part and the lower part, as well as the outer sides in the radial direction of the holder 602 are formed as open ends, so that a mounting platform 71 and an arm 72 of the raising and lowering unit 70 for raising or lowering the reagent-containing assembly 300 can be raised or lowered without contacting the holder 602 of the rack 600.

Figure 10:
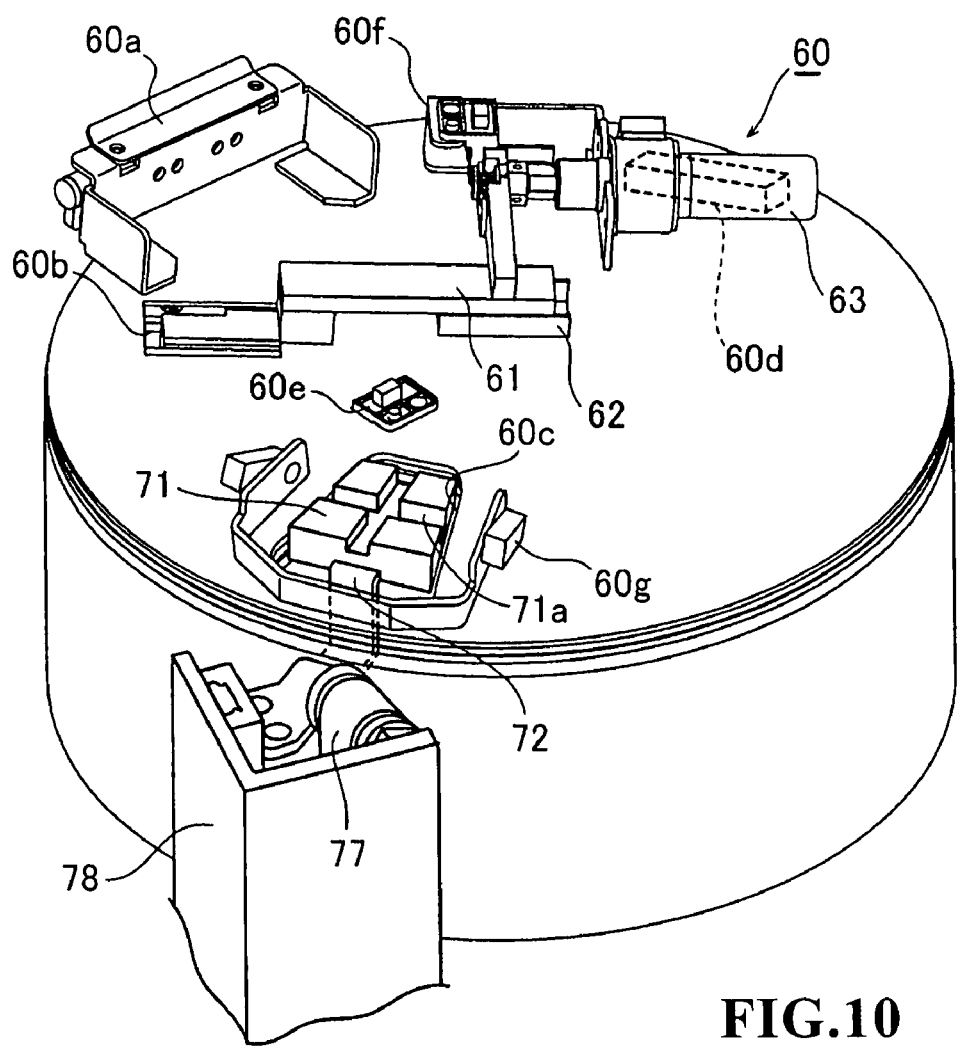
FIG. 10 is a perspective view showing the reagent installing unit shown in FIG. 6.
Figure 11:
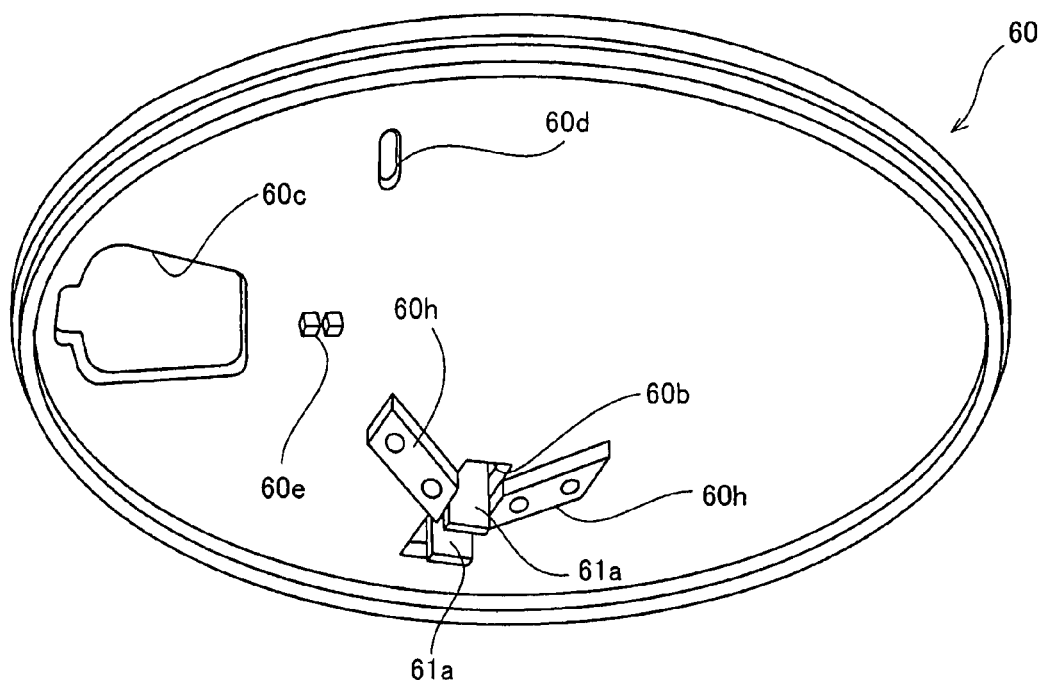
FIG. 11 is a perspective view showing a back surface of a lid of the reagent installing unit shown in FIG. 10.

As shown in FIG. 6, the lid 60 is attached in an openable and closable manner to the reagent holder 50 by way of a hinge part 60a. The lid 60 is configured to shield outside air so that the temperature in the reagent installing unit 7 is maintained at a low temperature (15° C.), and so as to enable the reagent in the reagent installing unit 7 to be suctioned from the outside and the reagent-containing assembly 300 to be placed in or taken out from the reagent installing unit 7. Specifically, as shown in FIGS. 10 and 11, the lid 60 has the hole 60b to be inserted with a pipette 9e of the reagent dispensing arm 9 when suctioning the reagent from the reagent container 310 (see FIGS. 16 and 17) of the reagent-containing assembly 300, and the input/output hole 60c for placing in or taking out the reagent-containing assembly 300 from the reagent installing unit 7 by the raising and lowering unit 70. Furthermore, the lid 60 includes an openable/closable member 61 for opening or closing a slide lid 322 (see FIGS. 16 and 17) of the reagent-containing assembly 300 arranged below the hole 60b, a linear movement guide 62 for slidably supporting the openable/closable member 61, and a stepping motor 63 for driving the openable/closable member 61 in a reciprocating manner. The lid 60 is arranged with a reflection sensor 60d for detecting whether or not the reagent-containing assembly 300 is held in the holder 602 of the rack 600, a transmissive origin detection sensor 60e for detecting an origin position of the rack 600, a transmissive sensor 60f for detecting an origin position of the openable/closable member 61, and a transmissive sensor 60g for detecting the reagent-containing assembly 300 mounted on the mounting platform 71 of the raising and lowering unit 70, to be hereinafter described. The sensor 60d is arranged on the front surface side of the lid 60 so that light can be irradiated towards the back surface side of the lid 60, and the origin detection sensor 60e is arranged on the back surface side of the lid 60. The sensor 60f is arranged on the front surface side of the lid 60. The sensor 60g is arranged on the front surface side of the lid 60 so as to cross the input/output hole 60c.

As shown in FIG. 11, the openable/closable member 61 includes a two-forked engagement strip 61a, similar to an openable/closable member 31. When the reagent-containing assembly 300 is arranged below the hole 60b with the slide lid 322 closed, the engagement strip 322a (see FIG. 16) of the slide lid 322 of the reagent-containing assembly 300 is positioned between the two-forked engagement strip 61a of the openable/closable member 61. A pair of guide strips 60h is attached in the vicinity of the hole 60b of the back surface of the lid 60. The pair of guide holes 60h has a function of contacting the engagement strip 322a of the slide lid 322 by the rotation of the rotation shaft 52 and guiding the same when arranged below the hole 60b with the slide lid 322 of the reagent-containing assembly 300 opened, thereby positioning the engagement strip 322a of the slide lid 322 between the two-forked engagement strip 61a of the openable/closable member 61.

The reflection sensor 60d is configured to detect whether or not the reagent-containing assembly 300 is held in the holder 602 of the rack 600. The transmissive origin detection sensor 30e has a function of detecting the origin detection strip 603 arranged in the rack 600 to detect the origin position of the rotating rack 600.

Figure 12:
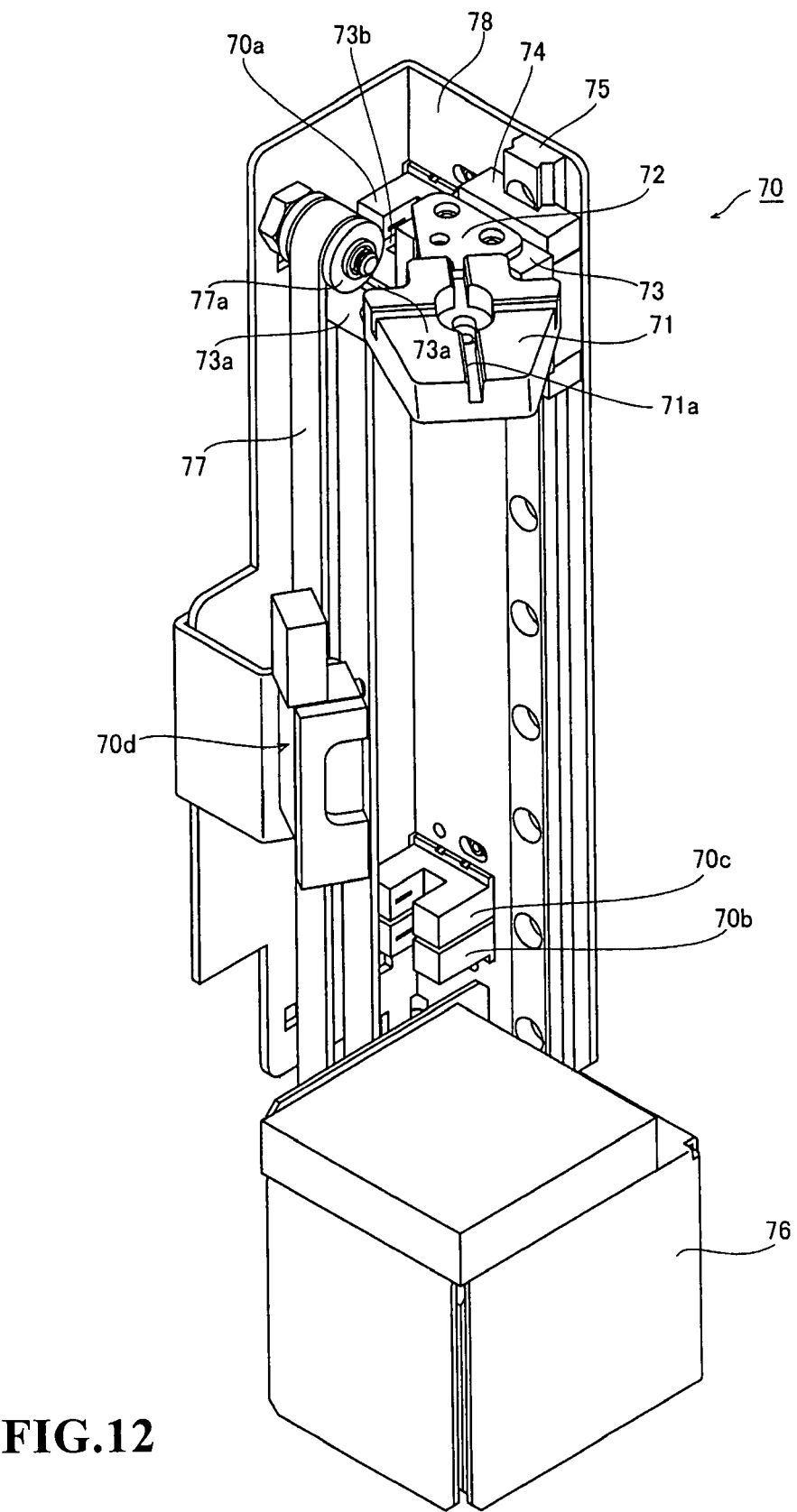
FIG. 12 is a perspective view showing a raising and lowering unit according to one embodiment.
Figure 13:
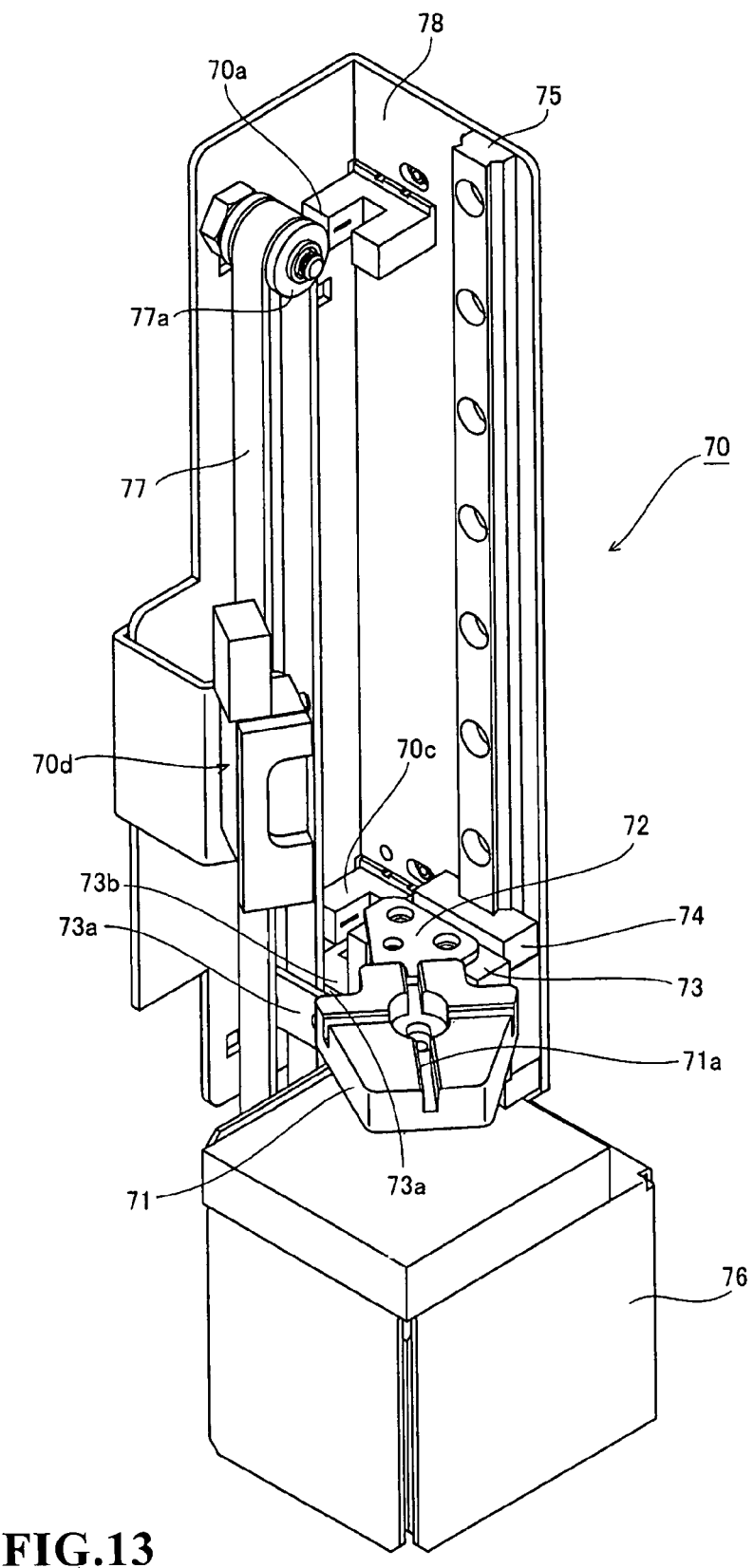
FIG. 13 is a perspective view showing the raising and lowering unit according to one embodiment.
Figure 14:
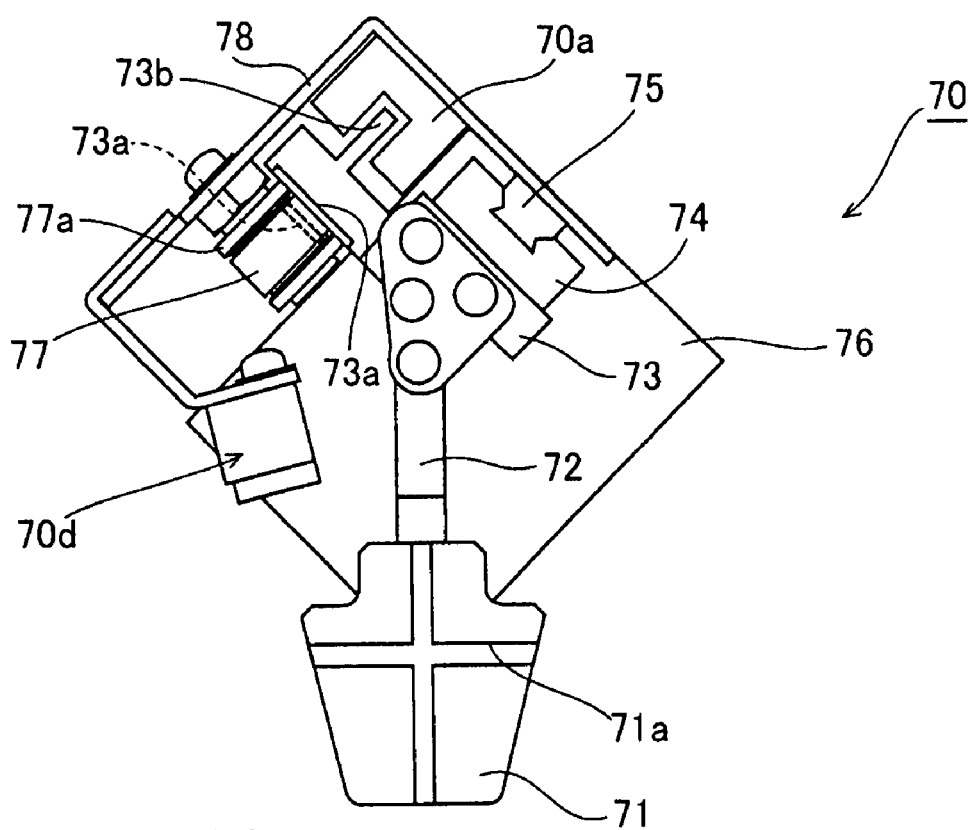
FIG. 14 is a plan view showing the raising and lowering unit according to one embodiment.

In the present embodiment, the raising and lowering unit 70 is arranged to place in and take out the reagent-containing assembly 300 in the reagent installing unit 7. As shown in FIGS. 12 to 14, the raising and lowering unit 70 includes the mounting platform 71 to be mounted with the reagent-containing assembly 300, the arm 72 for supporting the mounting platform 71, a supporting member 73 for supporting the arm 72, a linear movement guide including a slider 74 fixed with the supporting member 73 and a guide rail 75 for slidably supporting the slider 74 in the up and down direction, a motor 76, a belt 77 for transmitting the driving force of the motor 76, and a bracket 78. Three transmissive sensors 70a, 70b, and 70c as well as a reflection sensor 70d are attached to the bracket 78.

Figure 15:
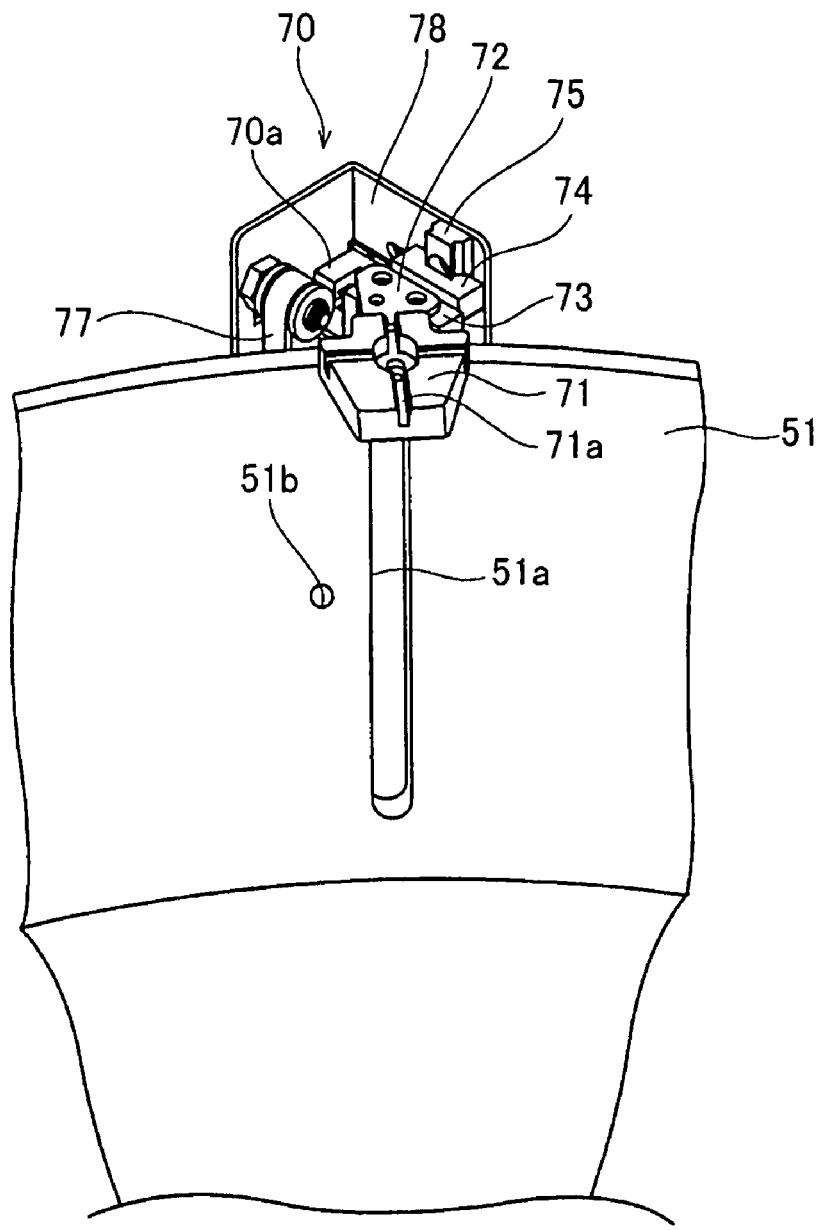
FIG. 15 is a perspective view showing a hole formed in an outer wall part of the reagent holder according to one embodiment.

The mounting platform 71 has a function of holding the reagent-containing assembly 300 in the holder 602 of the rack 600 by being lowered with the reagent-containing assembly 300 mounted thereon. The mounting platform 71 has a function of lifting the reagent-containing assembly 300 of the holder 602 and taking out the reagent-containing assembly 300 from the input/output hole 60c of the lid 60 by being raised from below the holder 602 holding the reagent-containing assembly 300. A cross-shaped groove 71a that engages with a rib 323*a* (see FIG. 18) arranged at the bottom 323 of the reagent-containing assembly 300 is formed in the mounting platform 71. As shown in FIG. 15, the arm 72 has a function of moving the mounting platform 71 in the up and down direction by the driving force of the motor 76 arranged exterior to the reagent holder 50 by way of a hole 51*a* extending in the up and down direction on the outer wall part 51.

A blocking member (not shown) made of elastic material arranged with a slit that corresponds to the hole 51*a* is attached to the hole 51*a*. The arm 72 supports the mounting platform 71 by way of the slit. The blocking member suppresses cold air in the container holder 50 from leaking outside from the hole 51*a* without inhibiting the movement of the arm 52.

As shown in FIG. 14, a two-forked fixing strip 73*a* arranged on the supporting member 73 is fixed to the belt 77 with the belt 77 in between. The driving force of the motor 76 is transmitted to the supporting member 73 via the belt 77. Furthermore, a detection strip 73*b* is arranged in a projecting manner on the supporting member 73. The position in the up and down direction of the mounting platform 71 is detected when the detection strip 73*b* is detected by the sensors 70*a*, 70*b*, and 70*c*. Specifically, when the detection strip 73*b* is detected by the sensor 70*a*, the mounting platform 71 is positioned at a mounting/retrieving position (top dead point) at which the reagent-containing assembly 300 can be mounted and retrieved. When the detection strip 73*b* is detected by the sensor 70*b*, the mounting platform 71 is positioned below (bottom dead point) the holder 602 of the rack 600. The mounting platform 71 is arranged below the reagent-containing assembly 300 held at the rack 600 when positioned at the bottom dead point, whereby the rack 600 can be rotated. A predetermined clearance region is provided between the rack 600 and the bottom dead point, and the sensor 70*c* detects the detection strip 73*b*. The control unit 2*a* can recognize that the mounting platform 71 is positioned in the clearance region between the holder 602 of rack 600 and the bottom dead point. Therefore, when the mounting platform 71 is positioned in the clearance region, the mounting platform 71 and the rack 600 are avoided from contacting each other when the rack 600 is rotated. The belt 77 is configured to be rotatably driven by a pulley (not shown) coaxially arranged on a rotation shaft (not shown) of the motor 76, and a pulley 77*a* arranged on the upper side.

The reflection sensor 70*d* detects the reagent-containing assembly 300 held in the holder 602 of the rack 600 by way of a hole 51*b* (see FIG. 15) arranged on the outer wall part 51 to monitor whether or not the replacement of the reagent-containing assembly 300 has been properly performed.

Figure 16:
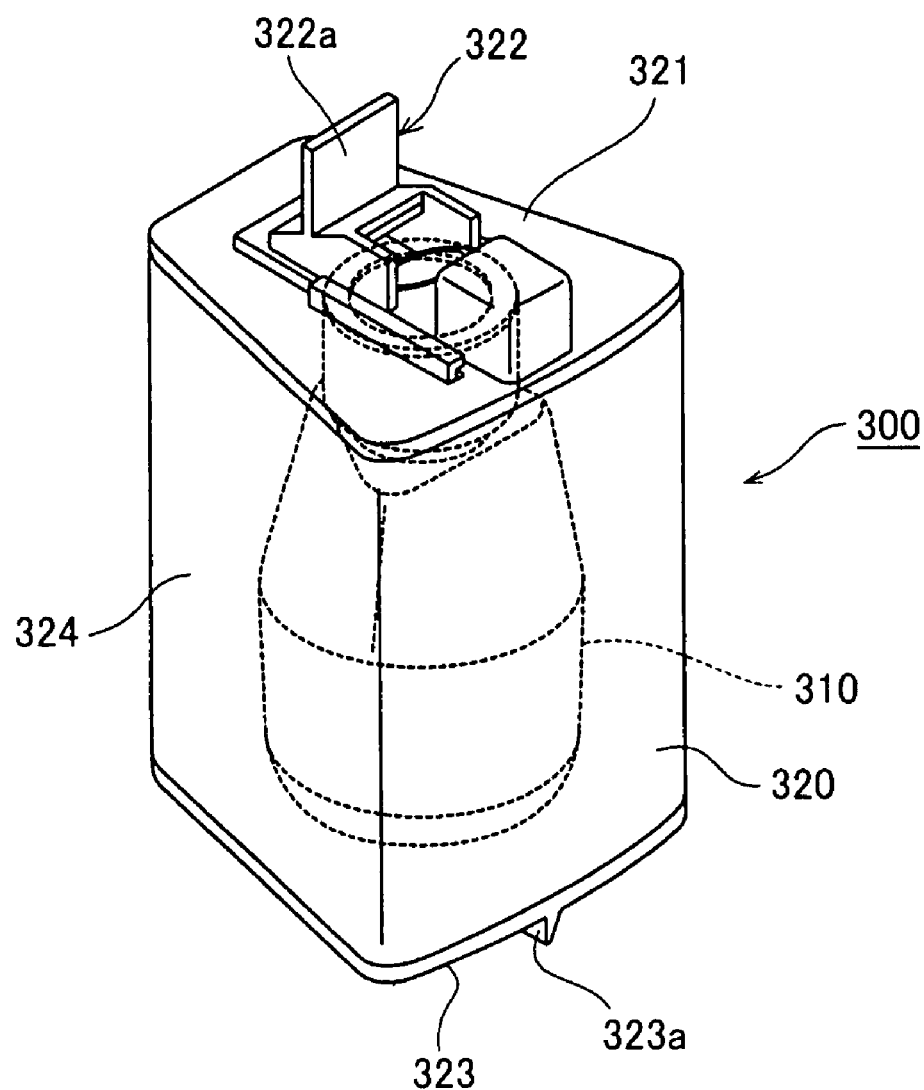
FIG. 16 is an outer appearance view of the reagent-containing assembly used in the immune analyzer according to one embodiment of the present invention.
Figure 17:
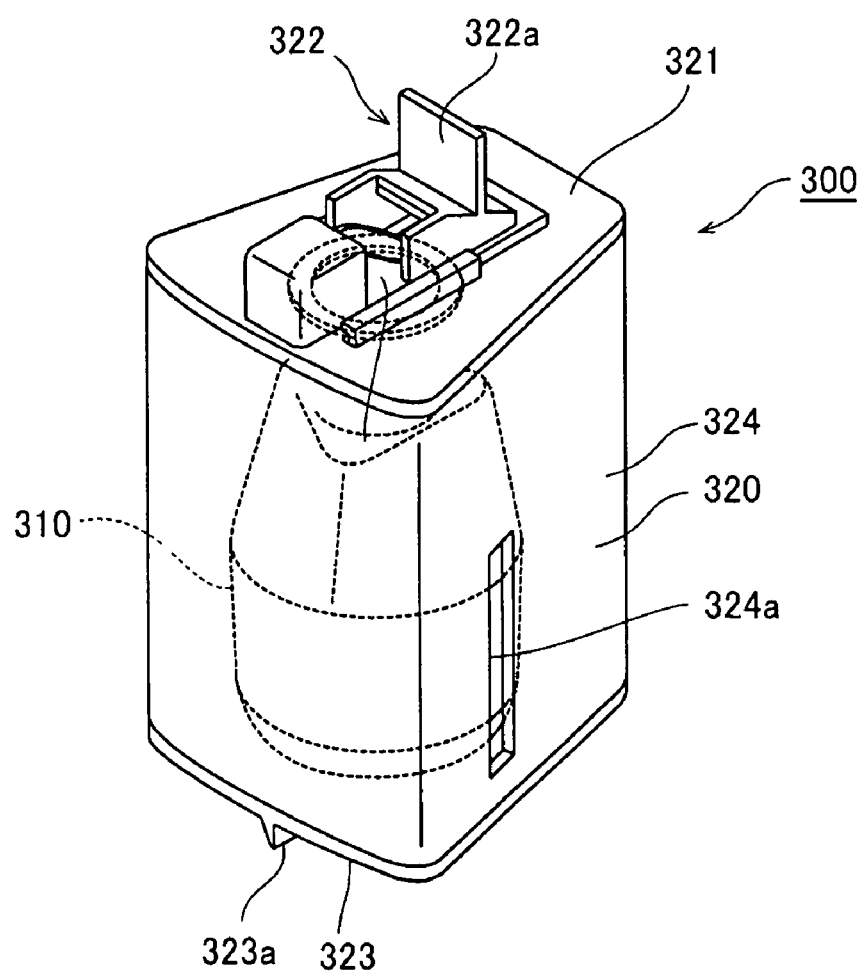
FIG. 17 is an outer appearance view of the reagent-containing assembly used in the immune analyzer according to one embodiment of the present invention.
Figure 18:
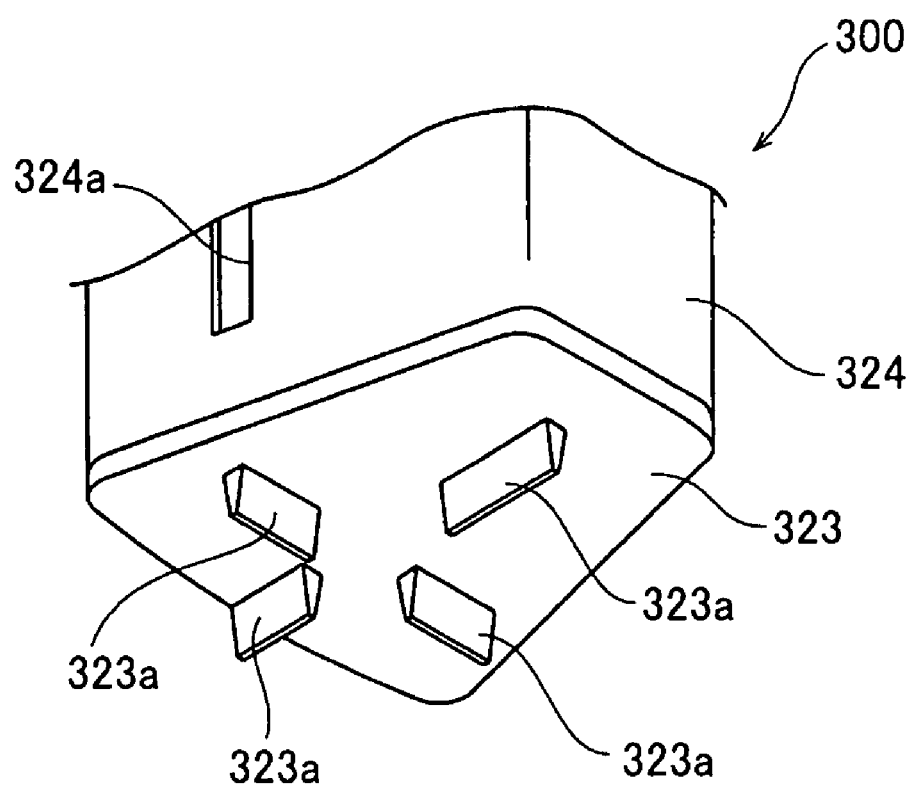
FIG. 18 is a perspective view showing the bottom of the reagent-containing assembly shown in FIG. 16.
Figure 19:
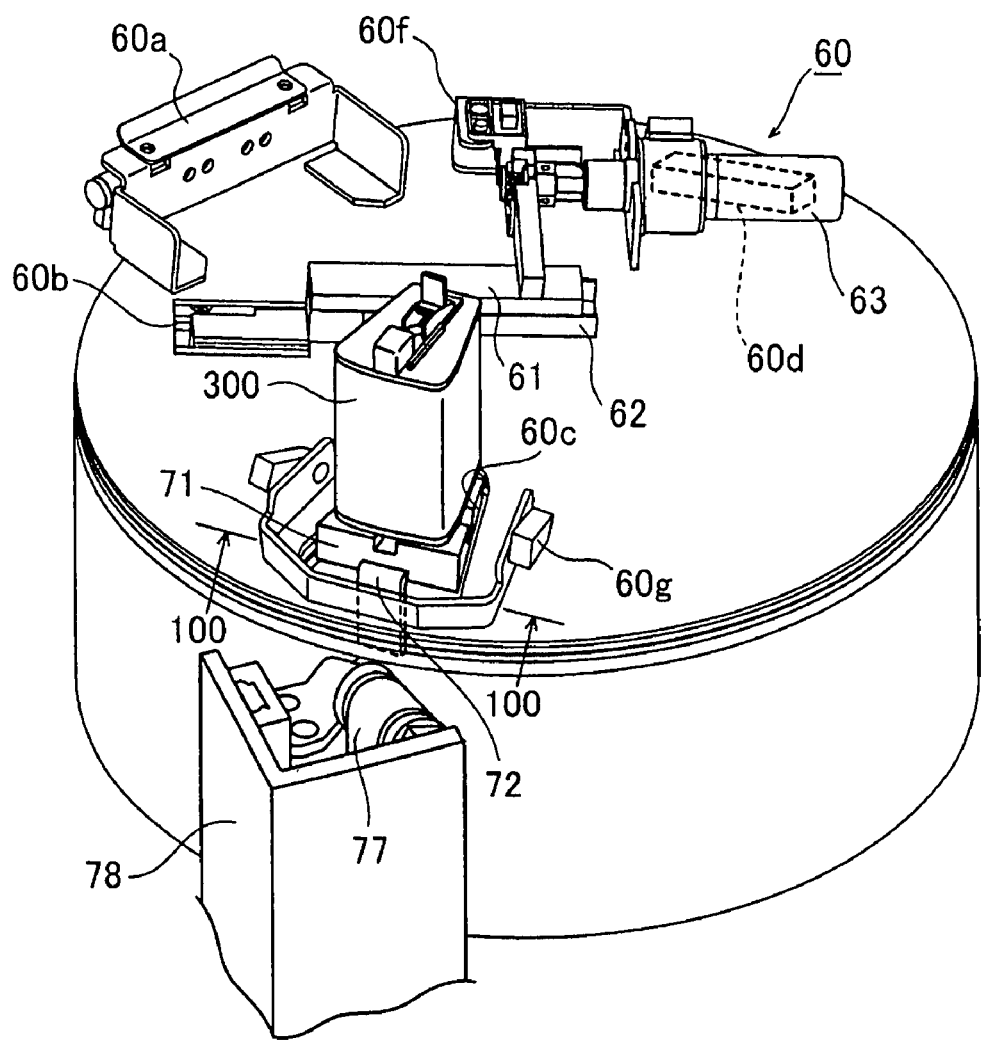
FIG. 19 is a perspective view showing a state in which a mounting platform of the raising and lowering unit of the immune analyzer according to one embodiment is positioned at a mounting/retrieving position.

As shown in FIGS. 16 to 18, the reagent-containing assembly 300 is made up of a reagent container 310 accommodating the R2 reagent, and a case 320 accommodating the reagent container 310. A slide lid 322 for sealing the reagent container 310 is formed on the upper surface 321 of the case 320. An engagement strip 322*a* for engaging the two-forked engagement strip 61*a* of the openable/closable member 61 is formed in the slide lid 322. A cross-shaped rib 323*a* that engages a groove 71*a* of the mounting platform 71 of the raising and lowering unit 70 is arranged in the bottom 323 of the case 320. A slit 324*a* (see FIG. 17) for visually recognizing the amount of reagent accommodated in the reagent container 310 is arranged on the side surface 324 of case 320.

The reagent installing unit 6 has a configuration similar to the reagent installing unit 7 except for that two openable/closable mechanisms are arranged on the lid 30 in correspondence to the reagent-containing assembly including two reagent containers of R1 reagent and the R2 reagent, and thus the description thereof will be omitted.

Addition, replacement, and retrieval operations of the reagent-containing assembly 300 in the reagent installing unit 7 of the immune analyzer 1 according to the present embodiment will now be described with reference to the FIGS. 8, 10, and 19 to 22.

As shown in FIG. 10, the mounting platform 71 is arranged at the mounting/retrieving position (state when the sensor 70*a* is ON) in the waiting state. When adding the reagent-containing assembly 300, the user first mounts the reagent-containing assembly 300 on the mounting platform 71, a shown in FIGS. 19 and 21.

Figure 20:
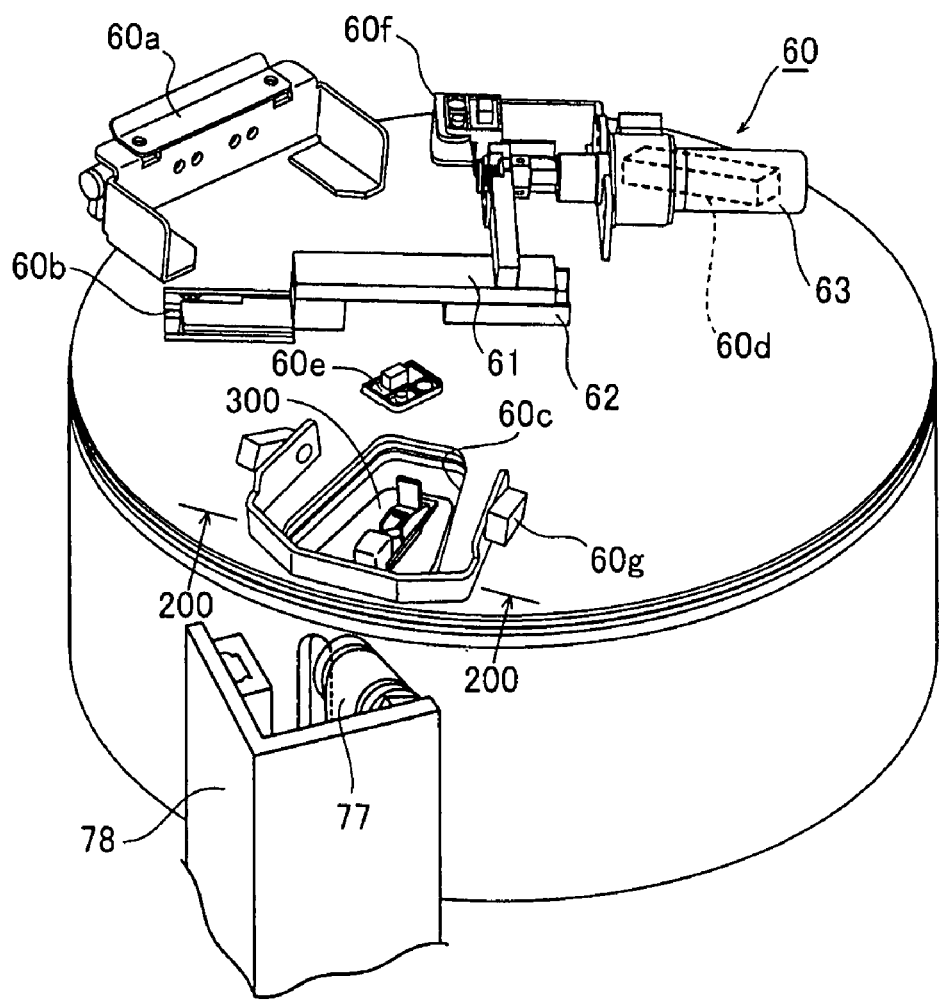
FIG. 20 is a perspective view showing a state in which the mounting platform of the raising and lowering unit of the immune analyzer according to one embodiment is positioned at a bottom dead point.
Figure 21:
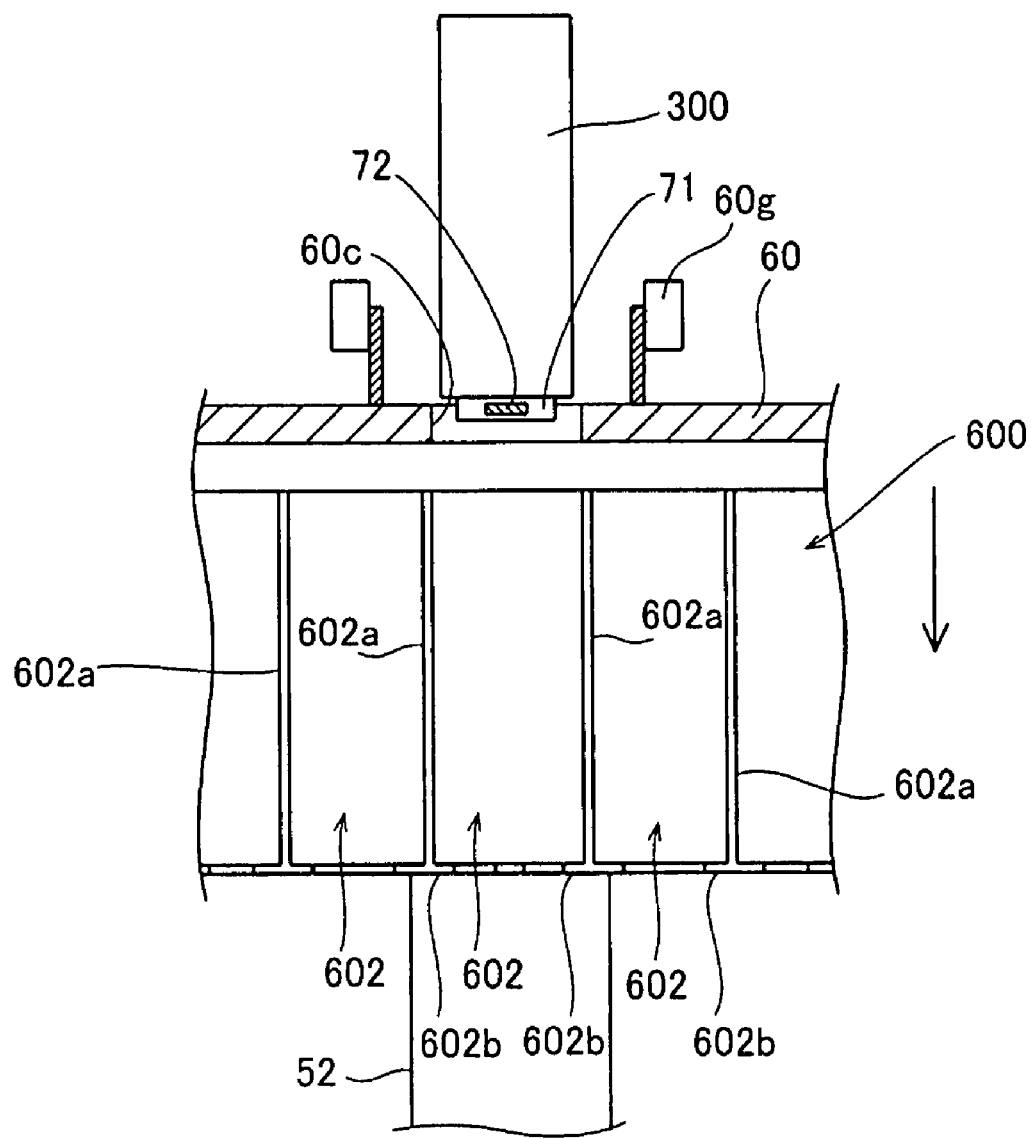
FIG. 21 is a cross sectional view taken along line 100-100 of FIG. 19.
Figure 22:
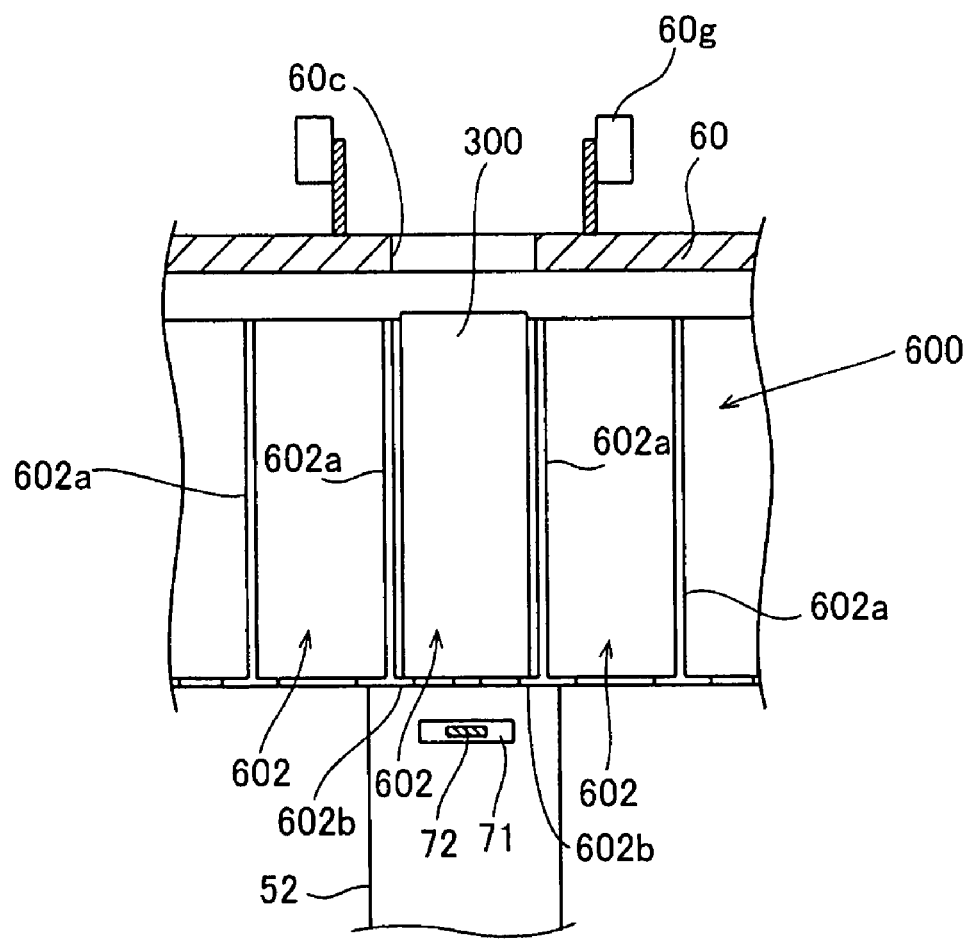
FIG. 22 is a cross sectional view taken along line 200-200 of FIG. 20.

The addition of the reagent-containing assembly 300 starts when the user instructs the addition of reagent by the control device 4 in this state. When the addition of the reagent-containing assembly 300 starts, the rack 600 is rotated by the drive of the stepping motor 53 (see FIG. 8), and the holder 602 not holding the reagent-containing assembly 300 is moved to below the input/output hole 60*c* of the lid 60. Subsequently, the movement to below the mounting platform 71 starts by the drive of the motor 76, as shown in FIG. 20. As shown in FIG. 22, when the mounting platform 71 passes through the supporting part 602*b* of the holder 602, the peripheral edge of the bottom 323 of the reagent-containing assembly 300 is supported by the supporting part 602*b* and the reagent-containing assembly 300 is held by the holder 602.

When the detection strip 73*b* is detected by the sensor 70*b*, the drive of the motor 76 is stopped. The rack 600 is rotated in this state by the drive of the stepping motor 53, and the holder 602 not holding the reagent-containing assembly 300 is moved to a waiting position below the input/output hole 60*c* (above the mounting platform 71 at the bottom dead point). The movement to the upper side of the mounting platform 71 then starts by the drive of the motor 76. The mounting platform 71 passes through the holder 602 not holding the reagent-containing assembly 300. The mounting platform 71 is then raised until the sensor 70*a* detects the detection strip 73*b*, and is arranged at the mounting/retrieving position. The addition of the reagent-containing assembly 300 is performed in such manner in the present embodiment.

When replacing the reagent-containing assembly 300, the user mounts the reagent-containing assembly 300 on the mounting platform 71 at the mounting/retrieving position, and then makes an instruction for replacement by the control device 4. The mounting platform 71 thereby lowers, the reagent-containing assembly 300 is held in the rack 600, and the mounting platform 71 moves to the bottom dead point (state when the sensor 70*b* is ON).

Thereafter, the rack 600 is rotated by the drive of the stepping motor 53, and the holder 602 holding the reagent-containing assembly 300 to be replaced is moved to below the input/output hole 60*c* (above the mounting platform 71 at the bottom dead point). The movement to the upper side of the mounting platform 71 then starts by the drive of the motor 76. The mounting platform 71 that is being raised lifts the reagent-containing assembly 300 supported by the supporting part 602*b* of the holder 602, and further rises. The mounting platform 71 is raised until the sensor 70*a* detects the detection strip 73*b*, and is then arranged at the mounting/retrieving position. The reagent-containing assembly 300 to be replaced is thereby retrieved to the outside of the reagent installing unit 7. The replacement of the reagent-containing assembly 300 is performed in this manner in the present embodiment.

When retrieving the reagent-containing assembly 300, instruction for retrieval is made by the control device 4. First, the rack 600 is rotated by the drive of the stepping motor 53, and the holder 602 not holding the reagent-containing assembly 300 is moved to below the input/output hole 60c (above the mounting platform 71 at the bottom dead point). The mounting platform 71 is then passed through the holder 602 not holding the reagent-containing assembly 300 and moved to the bottom dead point (state when the sensor 70b is ON). The rack 600 is then rotated, and the holder 602 holding the reagent-containing assembly 300 to be retrieved is moved to the upper side of the mounting platform 602. Thereafter, the mounting platform 71 is raised, and the reagent-containing assembly 300 to be retrieved is retrieved to the outside of the reagent installing unit 7.

The replacement, addition, and retrieval of the reagent-containing assembly in the reagent installing unit 6 are also performed similar to the reagent-containing assembly 300 in the reagent installing unit 7, and thus the description will be omitted.

The suctioning operation of suctioning the reagent from the reagent-containing assembly 300 by the pipette 9e of the reagent dispensing arm 9 according to the present embodiment will now be described with reference to FIGS. 1, 8, 11, 23, and 24.

Figure 23:
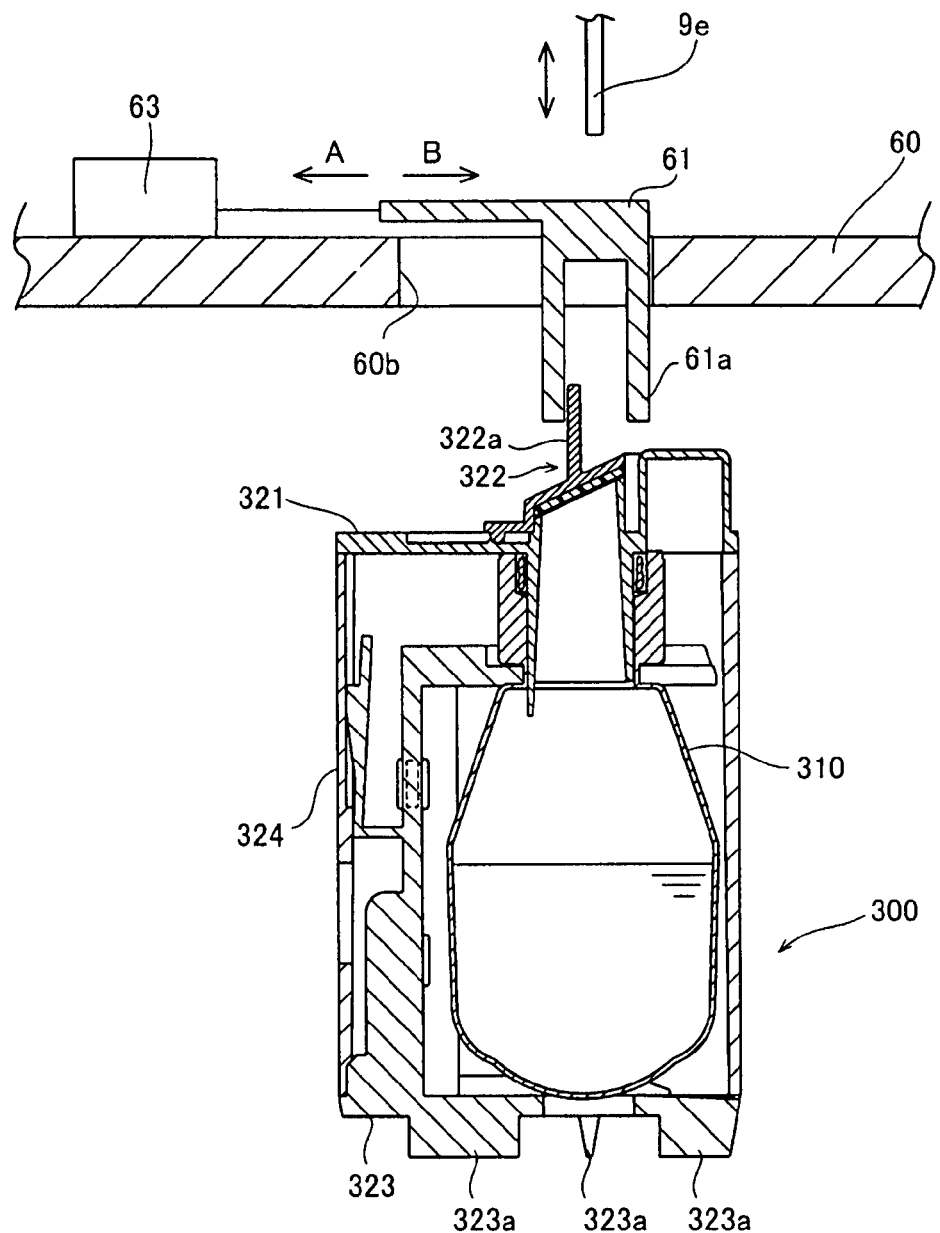
FIG. 23 is a cross sectional view showing a state in which a slide lid of the reagent-containing assembly is closed when suctioning the reagent.

The reagent-containing assembly 300 including the reagent container 310 accommodating the reagent to be suctioned is moved to below the hole 60b of the lid 60 by rotating the rack 600 in which the rotation shaft 52 (see FIG. 8) of the reagent holder 50 holds the reagent-containing assembly 300. The engagement strip 322a of the slide lid 322 is arranged between the two-forked engagement strip 61a of the openable/closable member 61 of the lid 60, as shown in FIG. 23, if the slide lid 322 of the reagent-containing assembly 300 is closed when the reagent-containing assembly 300 is moved to below the hole 60b of the lid 60. The engagement strip 322a of the slide lid 322 is guided by a guide strip 60h (see FIG. 11) arranged near the hole 60b of the lid 60 and arranged between the two-forked engagement strip 61a of the openable/closable member 611 if the slide lid 322 of the reagent-containing assembly 300 is opened when the reagent-containing assembly 300 is moved to below the hole 60b of the lid 60.

Figure 24:
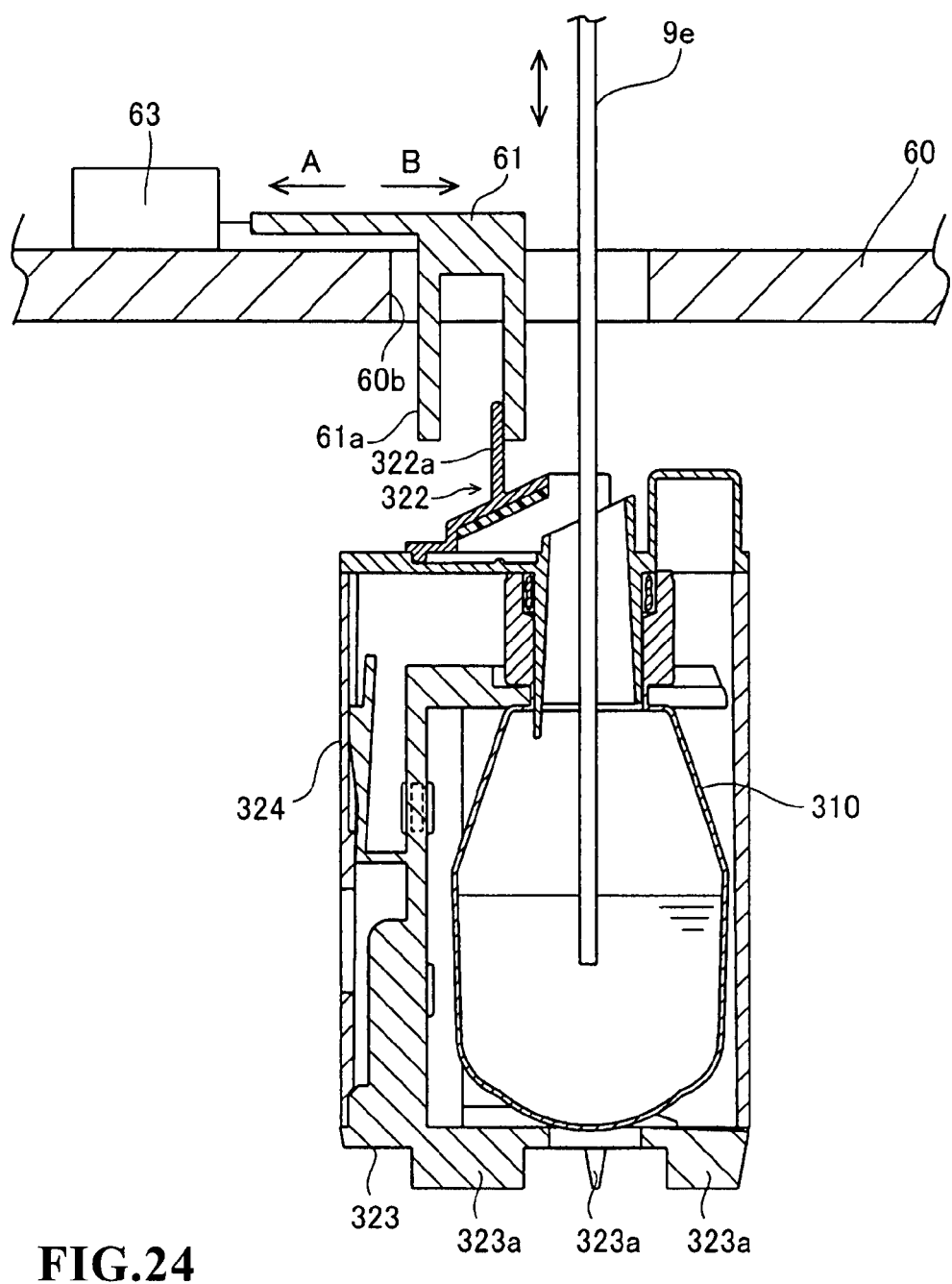
FIG. 24 is a cross sectional view showing a state in which the slide lid of the reagent-containing assembly is opened when suctioning the reagent.

If the openable/closable member 61 is sled in the direction of the arrow A by the stepping motor 63 in this state, the engagement strip 322a of the slide lid 322 is sled in a direction of the arrow A with the two-forked engagement strip 61a so that the slide lid 322 is in an opened state, as shown in FIG. 24. The pipette 9e of the reagent dispensing arm 9 then can be inserted into the reagent container 310. The pipette 9e is moved to the upper side of the hole 60b of the lid 60 through turning by the motor 9a and the drive transmitting part 9b, and the pipette 9e is lowered in the opened state of the slide lid 322 so that the pipette 9e can be inserted into the reagent container 310 through the hole 60b to suction the reagent.

The pipette 9e that has suctioned the reagent is raised and turned by the motor 9a and the drive transmitting part 9b, and moved to the upper side of the primary reaction unit 11 (see FIG. 1). The reagent suctioned from the reagent container 310 is then dispensed into the cuvette 150 of the primary reaction unit 11.

After the suctioning of the reagent is terminated, the turning member 61 is moved in a direction of the arrow B by the stepping motor 63, whereby the engagement strip 322a of the slide lid 322 is sled in the direction of the arrow B with the two-forked engagement strip 61a. The slide lid 322 is then closed, and the reagent is in the sealed state. The sealed state of the reagent is thus maintained even when the rack 600 is rotated and the reagent-containing assembly 300 is moved.

In the present embodiment, the mounting platform 71 is lowered with the reagent-containing assembly 300 mounted on the mounting platform 71 at the mounting/retrieving position (state when the sensor 70a is ON) to hold the reagent-containing assembly 300 at the holder 602 of the rack 600, as described above. The holder 602 of the rack 600 holding the reagent-containing assembly 300 is arranged on the upper side of the mounting platform 71 at the bottom dead point (state when the sensor 70b is ON) and the mounting platform 71 is raised to lift the reagent-containing assembly 300 and retrieve the reagent-containing assembly 300 to the outside of the reagent installing unit 7. According to such configuration, the immune analyzer 1 can be simplified and miniaturized. The user can mount the reagent-containing assembly 300 on the mounting platform 71 and retrieve the same at the mounting/retrieving position, and thus does not need to insert his/her hand into the reagent installing unit 7 when replacing the reagent-containing assembly 300. The reagent thus can be easily replaced.

Furthermore, in the present embodiment, the movement of the mounting platform 71 is executed by the motor 76 when instruction for replacement, addition, and retrieval of the reagent-containing assembly 300 is made by the control device 4, as described above, so that the reagent can be replaced when the user instructs replacement of the reagent by the control device 4 as desired.

In the present embodiment, the mounting platform 71 waits at the mounting/retrieving position until accepting instruction for replacement or addition of the reagent-containing assembly 300 by the control device 4, and when accepting instruction for replacement, addition, and retrieval, the raising and lowering unit 70 performs replacement, addition, and retrieval of the reagent-containing assembly 300, as described above, and thus the user can replace or add the reagent-containing assembly 300 without waiting for the mounting platform 71 to be raised to the mounting position since the mounting platform 71 is normally waiting at the mounting/retrieving position. Therefore, time from when the user instructs replacement and addition of the reagent-containing assembly 300 until a new reagent-containing assembly 300 is held by the holder 602 of the rack 600 can be reduced. The time of interrupting the analysis of the sample with replacement or addition of the reagent thus can be reduced.

Moreover, in the present embodiment, each of a plurality of reagent-containing assemblies 300 held in a circular ring form in the rack 600 can be arranged on a path of the mounting platform 71 by configuring the rack 600 holding the plurality of reagent-containing assemblies 300 in a circular ring form in a rotatable manner, as described above. The plurality of reagent-containing assemblies 300 held by the rack 600 thus can be replaced.

In the present embodiment, the supporting part 602b configured to support the bottom 323 of the reagent-containing assembly 300 and to pass the mounting platform 71 when the mounting platform 71 is raised is arranged in the rack 60, as described above, whereby the reagent-containing assembly 300 can be supported by the supporting part 602b with the lowering operation of the mounting platform 71, and the reagent-containing assembly 300 can be lifted and retrieved by the mounting platform 71 with the rising operation of the mounting platform 71. The reagent-containing assembly 300 mounted on the mounting platform 71 can be held by the rack 600 without separately arranging a mechanism for moving the reagent-containing assembly 300 between the rack 600 and the mounting platform 71.

In the present embodiment, the inside of the reagent installing unit 7 is cooled by the Peltier element, and the input/output hole 60c having a size that enables the reagent-containing assembly 300 to pass through is formed in the lid 60 so that the reagent-containing assembly 300 can be placed in and taken out from the input/output hole 60c, as described above, whereby the cooling by the Peltier element is efficiently performed while enabling replacement of the reagent-containing assembly 300.

The embodiments disclosed herein are illustrative and should not be construed as being restrictive. The scope of the invention is defined by the appended claims rather than by the description of the embodiments, and all changes that fall within meets and bounds of the claims, or equivalence of such meets and bounds are therefore intended to be embraced by the claims.

For instance, an example of applying the present invention to the immune analyzer 1 has been described in the above embodiment, but the present invention is not limited thereto, and may be applied to other analyzers such as biochemical analyzers and blood coagulation measurement devices.

In the above embodiment, a case in which the mounting platform 71 waits at the mounting/retrieving position and when accepting instruction for reagent replacement, the mounting platform 71 is lowered so that the rack 600 holds a new reagent-containing assembly 300, and thereafter, the mounting platform 71 is raised so that the old reagent-containing assembly 300 is retrieved has been described, but the present invention is not limited thereto. That is, the mounting platform 71 may wait below the rack 600, and when accepting the instruction for reagent replacement, the mounting platform 71 may be raised so that the old reagent-containing assembly 300 is retrieved, and thereafter, the mounting platform 71 may be lowered with the new reagent-containing assembly 300 mounted by the user so that the rack 600 holds the reagent-containing assembly 300.

In the above embodiment, a case in which only one raising and lowering unit 70 is arranged in the reagent installing unit 7 is described, but the present invention is not limited thereto, and two raising and lowering units may be arranged in the reagent installing unit. In this case, one of the two raising and lowering units is the raising and lowering unit dedicated for addition, and the other is the raising and lowering unit dedicated for retrieval.

In the above embodiment, a case in which the replacement, addition, and retrieval of the reagent-containing assembly 300 is performed by the raising and lowering unit 70 when the user makes an instruction for replacement by the control device 4 has been described, but the present invention is not limited thereto, and the used amount of reagent may be stored in the control unit, and the reagent-containing assembly to be replaced may be automatically retrieved when the used amount exceeds a predetermined amount and it is determined that the replacement of the reagent is necessary.

In the above embodiment, a case in which the reagent-containing assembly 300 is replaced through the input/output hole 60c formed in the lid 60 has been described, but the present invention is not limited thereto, and a shutter may be arranged at a position corresponding to the mounting platform of the lid, and the user may mount the reagent-containing assembly 300 on the shutter when carrying out the replacement. In such configuration, when instruction for replacement or addition of the reagent is made, the shutter opens so that the reagent-containing assembly is mounted on the mounting platform positioned immediately below the shutter. According to such configuration, the reagent in the reagent-containing assembly 300 can be more efficiently cooled.

In the above embodiment, the mounting position and the retrieving position of the reagent-containing assembly 300 are both the upper dead point of the mounting platform 71, but the two positions may be different positions.

In the present embodiment, the reagent-containing assembly 300 has the reagent container 310 accommodated in the case 320, and the R2 reagent accommodated in the reagent container 310, but the reagent container 310 does not need to be accommodated in the case 320, and the reagent container 310 itself may be the reagent-containing assembly.

What is claimed is:

1. An analyzer comprising:
    a reagent suction unit for suctioning reagent from a reagent container;
    an analyzing unit for analyzing an analyzing specimen comprising a sample and the reagent;
    a container holder configured to hold a plurality of reagent containers, wherein the container holder comprises:
        a plurality of holding regions for holding the reagent containers; and
        a reagent container holding portion corresponding to each holding region, wherein each reagent container holding portion defines a bottom of the corresponding holding region; and
    a container raising and lowering unit comprising a mounting platform, wherein the container raising and lowering unit is configured to raise and lower the mounting platform through any one of the plurality of holding regions between a first position at which the reagent container is mounted on and retrieved from the mounting platform and a second position at which the reagent container is brought into contact with the reagent container holding portion corresponding to the holding region through which the mounting platform is raised and lowered.

2. The analyzer according to claim 1, wherein the container raising and lowering unit further comprises a driving source configured for raising and lowering the mounting platform.

3. The analyzer according to claim 1, wherein the container holder is a rack for holding the plurality of reagent containers in a circular ring form.

4. The analyzer according to claim 3, wherein the rack comprises,
    a plurality of partition plates, wherein each of the plurality of holding regions is defined by an area between adjacent partition plates, and
    each of the container holding portions being positioned between adjacent partition plates.

5. The analyzer according to claim 4, wherein each of the container holding portions comprises a projecting member projecting in a horizontal direction from the adjacent partition plates.

6. The analyzer according to claim 1, wherein the container holding portion holds part of the bottom surface of the reagent container.

7. An analyzer comprising:
    a reagent suction unit for suctioning reagent from a reagent container;
    an analyzing unit for analyzing an analyzing specimen comprising a sample and the reagent;
    a container holder configured to hold a plurality of reagent containers in a circular ring form;
    a container raising and lowering unit configured for executing a mounting operation of mounting the reagent container on the container holder by lowering the reagent container from a mounting position at which a reagent container is mounted on the container raising and lowering unit, and a raising operation of raising the reagent container to a retrieving position above the container holder, the retrieving position being the same as the mounting position; and a rotation unit configured for moving at least one of the plurality of reagent containers to a raise waiting position below the retrieving position, at which the container raising and lowering unit raises the reagent container to the retrieving position, by rotating the plurality of reagent containers held by the container holder.

8. The analyzer according to claim 7, wherein the retrieving position is the highest position of the reagent container raised by the container raising and lowering unit.

9. The analyzer according to claim 7, wherein the container raising and lowering unit comprises,
a mounting platform on which at least one of the plurality of reagent containers is mounted; and
a driving source for moving the mounting platform to the raise waiting position and the retrieving position.

10. The analyzer according to claim 9, further comprising a replacement instruction accepting means for accepting an instruction for reagent replacement; wherein
the driving source executes the movement of the mounting platform when the replacement instruction accepting means accepts the instruction for reagent replacement.

11. The analyzer according to claim 10, wherein
the mounting platform is arranged at the retrieving position until the replacement instruction accepting means accepts the instruction for reagent replacement; and
the driving source moves the mounting platform from the retrieving position to the raise waiting position, and then moves the mounting platform from the raise waiting position to the retrieving position when the replacement instruction accepting means accepts the instruction for reagent replacement.

12. The analyzer according to claim 9, wherein
the container holder comprises a container holding portion configured to hold the bottom surface of the reagent container, and allow the mounting platform to pass through when the mounting platform is raised and lowered; and
the container raising and lowering unit allows the reagent container to be held by the container holding portion when the mounting platform mounted with the reagent container is lowered to below the container holding portion, and the reagent container to be retrieved from the container holding portion when the mounting platform is raised from below the container holding portion holding the reagent container.

13. The analyzer according to claim 9, further comprising:
a cooling unit for cooling the reagent container held by the container holder; and
an accommodating unit, comprising a container opening of a size that allows the reagent container to pass through, for accommodating the cooling unit, the container holder, and the reagent container held by the container holder; wherein
the driving source moves the mounting platform so that the reagent container passes through the container opening.

14. An analyzer comprising:
a reagent suction unit for suctioning reagent from a reagent container;
an analyzing unit for analyzing an analyzing specimen comprising a sample and the reagent;
a container holder configured to hold a plurality of reagent containers;
a mounting platform on which at least one of the plurality of reagent containers is mounted, wherein the container holder has an area through which the mounting platform passes in the up and down direction; and
a driving source for moving the mounting platform to a first position, above the container holder, at which a reagent container is mounted on and retrieved from the mounting platform, and a second position, below the first position, at which a reagent container is held by the container holder.

15. The analyzer according to claim 14, wherein the second position is vertically below the first position.

16. The analyzer according to claim 14, wherein the driving source moves the mounting platform only in an up and down direction.

17. The analyzer according to claim 14, wherein the reagent container is held by the container holder when the driving source lowers the mounting platform.

18. The analyzer according to claim 14, wherein the container holder has an area through which the mounting platform passes in the up and down direction.

19. The analyzer according to claim 14, wherein the container holder is a rack for holding the plurality of reagent containers in a circular ring form.

* * * * *